US007745111B2

(12) United States Patent
Abdullah et al.

(10) Patent No.: US 7,745,111 B2
(45) Date of Patent: Jun. 29, 2010

(54) MOLECULAR MARKERS OF PLANT EMBRYOGENESIS

(75) Inventors: Meilina Ong Abdullah, Kajang Selangor (MY); Harikrishna Kulaveerasingam, Selangor (MY)

(73) Assignee: Malaysian Palm Oil Board, Kajang Selangor (MY)

( * ) Notice: Subject to any disclaimer, the term of this patent is extended or adjusted under 35 U.S.C. 154(b) by 1749 days.

(21) Appl. No.: 10/028,346

(22) Filed: Dec. 20, 2001

(65) Prior Publication Data
US 2010/0120151 A1    May 13, 2010

(30) Foreign Application Priority Data
Dec. 20, 2000    (AU) .................................... PR2213

(51) Int. Cl.
*C12N 15/29* (2006.01)
*C12N 15/82* (2006.01)
*C12Q 1/68* (2006.01)

(52) U.S. Cl. ...................... 435/6; 536/23.6; 435/320.1; 435/419; 435/252.3; 435/69.1; 435/468

(58) Field of Classification Search ....................... None
See application file for complete search history.

(56) References Cited

FOREIGN PATENT DOCUMENTS

WO    WO 98/43666    10/1998

OTHER PUBLICATIONS

Lewis M.L. et al. FePer 1, a gene encoding an evolutionarily conserved 1-Cys peroxiredoxin in buckwheat (*Fagopyrum esculentum* Moench), is expressed in a seed-specific manner and induced during seed germination. Gene. Apr. 4, 2000;246(1-2):81-91.*
Lee K.O. et al. Rice 1Cys-peroxiredoxin over-expressed in transgenic tobacco does not maintain dormancy but enhances antioxidant activity. FEBS Lett. Dec. 8, 2000;486(2):103-6.*
Parveez G.K.A. et al. Transgenic oil PALM: production and projection. Biochemical Society Transactions, 2000, 28(6):969-972.*
Lewis M.L. et al. GenBank Accession No. AF191099, *Fagopyrum esculentum* 1-Cys peroxiredoxin (Per1) mRNA, complete cds., Apr. 24, 2000.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
Hornung E. et al. Conversion of cucumber linoleate 13-lipoxygenase to a 9-lipoxygenating species by site-directed mutagenesis. Proc Natl Acad Sci USA. Mar. 30, 1999;96(7):4192-7.*
Gillespie D. The magic and challenge of DNA probes as diagnostic reagents. Vet Microbiol. Sep. 1990;24(3-4):217-33. Review.*
Stacy R.A. et al. A peroxiredoxin antioxidant is encoded by a dormancy-related gene, Per1, expressed during late development in the aleurone and embryo of barley grains. Plant Molecular Biology. 1996, 31: 1205-1216.*
Lee K.O. et al., "Rice 1Cys-Peroxiredoxin Over-Expressed in Transgenic Tobacco Does Not Maintain Dormancy but Enhances Antioxidant Activity", *FEBS Letters* 486(2):103-106 (2000).
Lewis M.L. et al., "FePer 1, a Gene Encoding an Evolutionarily Conserved 1-Cys Peroxiredoxin in Buckwheat (*Fagopyrum Esculentum* Moench), is Expressed in a Seed-Specific Manner and Induced During Seed Germination", *Gene* 246(1-2):81-91 (2000).
Stacy R.A.P. et al., "A Peroxiredoxin Antioxidant is Encoded by a Dormancy-Related Gene, *Per1*, Expressed During Late Development in the Aleurone and Embryo of Barley Grains", *Plant Molecular Biology* 31(6):1205-1216 (1996), XP-001076660.
Aalen R.B., EMBL Database Accession No. X76605 (1994), XP-002198603.
Parveez G.K.A. et al., "Transgenic Oil Palm: Production and Projection", *Biochemical Society Transactions* 28(6):969-972 (2000), XP-002198601.
Young T.E. et al., "Regulation of Programmed Cell Death in Maize Endosperm by Abscisic Acid", *Plant Molecular Biology* 42(2):397-414 (2000), XP-002198602.
Altschul, S. F., et al., "Gapped BLAST and PSI-BLAST: a new generation of protein database search programs", *Nucleic Acids Research* 25(17): 3389-3402 (1997).
Ausubel, F. M., et al., "Current Protocols in Molecular Biology", *Current Protocols in Molecular Biology*, Chapter 15, vol. 3 (1994-1998).
Choi, H. J., et al., "Crystal structure of a novel human peroxidase enzyme at 2.0A resolution", *Nature Structural Biology* 5(5): 400-406 (1998).
Dudits, D., et al., "Molecular Biology of Somatic Embryogenesis", *In Vitro Embryogenesis in Plants*, pp. 267-308 (1995).

(Continued)

*Primary Examiner*—Cynthia Collins
(74) *Attorney, Agent, or Firm*—Scully, Scott, Murphy & Presser, P.C.

(57) ABSTRACT

The present invention relates generally to a molecular marker for a plant physiological process and more particularly for plant embryogenesis. The molecular marker is, in one form, a genetic sequence from a monocot plant such as but not limited to oil-palm plants. In another form, the molecular marker is a polypeptide encoded by said genetic sequence. More particularly, the molecular marker of the present invention enables embryogenic tissue to be detected in vitro. The early detection of embryogenic tissue enables non-embryogenic tissue to be discarded. The ability to detect embryogenesis facilitates maximization of embryogenic potential. The present invention further contemplates a molecular marker comprising in one form a sequence of nucleotides encoding an antioxidant or in another form a sequence of amino acids defining a polypeptide having antioxidant activity. The antioxidant according to this aspect of the present invention is particularly useful in tablet or cream form as an anti-aging agent. The molecular markers of the present invention therefore also have uses in the inhibition or retardation of apoptotic processes. Such an effect has benefits in both plant and animal cells. The present invention further contemplates a promoter sequence encoding the molecular marker and its use in generating male sterile plants.

23 Claims, 7 Drawing Sheets

OTHER PUBLICATIONS

Goldmark, P. J., et al., "Cloning and expression of an embryo-specific mRNA up-regulated in hydrated dormant seeds", *Plant Molecular Biology 19*: 433-441 (1992), XP-001076662.

Heck, G. R., et al., "AGL15, a MADS Domain Protein Expressed in Developing Embryos", *The Plant Cell* 7: 1271-1282 (1995), XP-002053995.

Pannetier, C., et al., "Neoformation of young *Elaeis guineensis* plants from primary calluses obtained on leaf fragments culture in vitro", *Oleagineux 36*(3): 119-122 (1981).

Turnham, E., et al., "The use of acetyl-CoA carboxylase activity and changes in wall composition as measures of embryogenesis in tissue cultures of oil palm (*Elaeis guineensis*)", *Biochem. J.* (208): 323-332 (1982); and.

Wooi, K. C., "Oil Palm Tissue Culture—Current Practice and Constraints", *Proceedings of the 1993 ISOPB International Symposium on Recent Developments in Oil Palm Tissue Culture and Biotechnology*, Palm Oil Research Institute of Malaysia, Kuala Lumpur, pp. 21-32 (1993).

* cited by examiner

```
  3    CAC GAG GTG AAT CGG AGC CGT TGA AAG ATG CCG GGG CTA ACG ATC   47
  0                                            M   P   G   L   T   I   14

48    GGC GAC ACG ATC CCG AAC CTG GAG GTG GAG ACC ACG CAC GGG AAG   92
 15     G   D   T   I   P   N   L   E   V   E   T   T   H   G   K   29

93    ATC CGG ATC CAC GAC TAC GTC GGC GAT GGT TGG GCC ATC ATC TTC  137
 30     I   R   I   H   D   Y   V   G   D   G   W   A   I   I   F   44

138    TCC CAT CCC GCG GAT TTC ACA CCC GTG TGC ACG ACG GAG CTG GGG  182
 45     S   H   P   A   D   F   T   P   V   C   T   T   E   L   G   59

183    AAG ATG GCG GCG TAC GCG GAG GAG TTC GAG AAA AGA GGG GTG AAG  227
 60     K   M   A   A   Y   A   E   E   F   E   K   R   G   V   K   74

228    CTG CTA GGC ATC TCC TGC GAC GAT GTC AAG TGC CAC ATG GAA TGG  272
 75     L   L   G   I   S   C   D   D   V   K   C   H   M   E   W   89

273    ATC AAA GAC GTC GAG GCC TAC ACG CCC GGA TGT CGC GTA ACA TAT  317
 90     I   K   D   V   E   A   Y   T   P   G   C   R   V   T   Y  104

318    CCA ATT GTA GCC GAC CCC AAG AGG GAG GTG ATC AAA CTG CTG AAC  362
105     P   I   V   A   D   P   K   R   E   V   I   K   L   L   N  119

363    ATG GTA GAC CCT GAG GAG AAG GAC TCA AAT GGG AAC CAG CTC CCG  407
120     M   V   D   P   E   E   K   D   S   N   G   N   Q   L   P  134

408    TCA CGG GCC CTT CAT ATA GTG GGC CCT GAT AAG AAG GTT AAG CTG  452
135     S   R   A   L   H   I   V   G   P   D   K   K   V   K   L  149

453    AGC TTT CTG TAC CCG GCG TCG ACG GGG CGG AAC ATG GAG GAG GTG  497
150     S   F   L   Y   P   A   S   T   G   R   N   M   E   E   V  164

498    GTC AGG GTG TTG GAG TCG CTT CAG AAG ACG ATC AAG TAT AAG GTG  542
165     V   R   V   L   E   S   L   Q   K   T   I   K   Y   K   V  179

543    GCG ACC CCA GCG AAC TGG AAA CCG GGG GAG CCG GTG GTG ATC TCG  587
180     A   T   P   A   N   W   K   P   G   E   P   V   V   I   S  194

588    CCC GAG CGT GTC CAA TGA GGA GGC CAA GCA GAT GTT CCC GCA GGG  632
195     P   E   R   V   Q   *

633    AGT TGA GAA TGT GAA TCT CCC ATC GAA GAA GGA TTA CCT CCG CTT  677

678    CAC AAA AGT CTA ATG TTG TTG GGC CGT CCG TGA TAT GTT CAT AAG  722

723    TGG TTT CTG GGG CCC GAC TGT ATA CTG TGT TGT CGT GTT ATA TGT  767

768    TTG TGT TGG TAT CAT GTA GTT TGT GCC TTA GGG GAG TTT GGA TAT  812

813    TAA TTT GTA GTT TAT GTT AAT TAT TAA AGT TTT TAC CAT GAG ATT  857

858    AAA AAA AAA AAA AAA AAA     875
```

Figure 3

```
OPEm1       ------------------------------MPGLT--------------------
HvPer1      ------------------------------MPGLT--------------------
AtPer1      ------------------------------MPGIT--------------------
C2CPRX      MASVASSTTLISSSASVLPATKSSLLPSPSLSFLPTLSSPSPSASLRSLVPLPSPQSASS
                                          :*  ::

OPEm1       ----------------IGDTIPNLEVETTHG-------KIRIHDYVGDGWAIIFSHPADF
HvPer1      ----------------IGDTVPNLELDSTHG-------KIRIHDYVGNGYVILFSHPGDF
AtPer1      ----------------LGDTVPNLEVETTHD-------KFKLHDYFANSWTVLFSHPGDF
C2CPRX      SRRSFAVKGQTDDLPLVGNKAPDFEAEGVFDQEFIKFIKVKLSDYIGKKYVILFFLPLDF
                            :*:. *::*  :   ...    *.:: **... :.::*  *  **

OPEm1       TPVCTTELGKMAAYAEEFEKRGVKLLGISCD--DVKCHMEWIKDVEAYTPGCRVTYPIVA
HvPer1      TPVCTTELAAMANYAKEFEKRGVKLLGISCD--DVQSHKEWTKDIEAYKPGSKVTYPIMA
AtPer1      TPVCTTELGAMAKYAHEFDKRGVKLLGLSCD--DVQSHKDWIKDIEAFNHGSKVNYPIIA
C2CPRX      TFVCPTEITAFSDRYAEFEKLNTEVLGVSVDSVSVFSHLAGVQTDRKFGGLGDLNYPLIS
            * **.**:   ::      **:*  ..::**:* *  .*  .*       :  . :    :.**:::

OPEm1       DPKREVIKLLNMVDPEEKDSNGNQLPSRALHIVGPDKKVKLSFLYPASTGRNMEEVVRVL
HvPer1      DPDRSAIKQLNMVDPDEKDAQG-QLPSRTLHIVGPDKVVKLSFLYPSCTGRNMDEVVRAV
AtPer1      DPNKEIIPQLNMIDPIE---NG---PSRALHIVGPDSKIKLSFLYPSTTGRNMDEVLRAL
C2CPRX      DVTKSISKSFGVLIHDQ----G--IALRGLFIIDKEGVIQHSTIN-LGIGRSVDETMRTL
            *  :.     :.::    :     *   .  *  *.*:. :   ::  * :     **.::*.:*.:

OPEm1       ESLQKTIKY--KVATPANWKPGEPVVISP----ERVQ-----------------------
HvPer1      DSLLTAAKH--KVATPANWKPGECVVIAPGVSDEEAKKMFPQGFETADLPSKKGYLRFTK
AtPer1      DSLLMASKHNNKIATPVNWKPDQPVVISPAVSDEEAKKMFPQGFKTADLPSKKGYLRHTE
C2CPRX      QALQYIQEGP-GEVCPAGWKPGEKSMKPDP---KLSKELFSAI-----------------
            ::*    :      . *...***.:  : .              :  :

OPEm1       --
HvPer1      V-
AtPer1      VS
C2CPRX      --
```

Figure 5

```
OPEm1    MPGLTIGDTIPNLEVETTHGKIRIHDYVGDGWAIIFSHPADFTPVCTTELGKMAAYAEEF
HvPer1   MPGLTIGDTVPNLELDSTHGKIRIHDYVGNGYVILFSHPGDFTPVCTTELAAMANYAKEF
AtPer1   MPGITLGDTVPNLEVETTHDKFKLHDYFANSWTVLFSHPGDFTPVCTTELGAMAKYAHEF
         ***:*:***:****:::**.*:::***..:..:.::****.**********. ** **.**

OPEm1    EKRGVKLLGISCDDVKCHMEWIKDVEAYTPGCRVTYPIVADPKREVIKLLNMVDPEEKDS
HvPer1   EKRGVKLLGISCDDVQSHKEWTKDIEAYKPGSKVTYPIMADPDRSAIKQLNMVDPDEKDA
AtPer1   DKRGVKLLGLSCDDVQSHKDWIKDIEAFNHGSKVNYPIIADPNKEIIPQLNMIDPIE---
         :********:*****:.* :* **:**:. *.:*.***:***.:. *   ***:** *

OPEm1    NGNQLPSRALHIVGPDKKVKLSFLYPASTGRNMEEVVRVLESLQKTIKY--KVATPANWK
HvPer1   QG-QLPSRTLHIVGPDKVVKLSFLYPSCTGRNMDEVVRAVDSLLTAAKH--KVATPANWK
AtPer1   NG---PSRALHIVGPDSKIKLSFLYPSTTGRNMDEVLRALDSLLMASKHNNKIATPVNWK
         :*   ***:*******. :*******:  *****:**:**:.::**   : *:  *:***.***

OPEm1    PGEPVVISP----ERVQ-------------------------
HvPer1   PGECVVIAPGVSDEEAKKMFPQGFETADLPSKKGYLRFTKV-
AtPer1   PDQPVVISPAVSDEEAKKMFPQGFKTADLPSKKGYLRHTEVS
         *.: ***:*    *...:
```

Figure 6

SEQUENCE LISTING

<160> NUMBER OF SEQ ID NOS: 9

<210> SEQ ID NO 1
<211> LENGTH: 573
<212> TYPE: DNA
<213> ORGANISM: oil palm
<220> FEATURE:
<221> NAME/KEY: CDS
<222> LOCATION: (1)..(573)

<400> SEQUENCE: 1

| atg | ccg | ggg | cta | acg | atc | ggc | gac | acg | atc | ccg | aac | ctg | gag | gtg | gag | 48 |
|---|---|---|---|---|---|---|---|---|---|---|---|---|---|---|---|---|
| Met | Pro | Gly | Leu | Thr | Ile | Gly | Asp | Thr | Ile | Pro | Asn | Leu | Glu | Val | Glu | |
| 1 | | | | 5 | | | | | 10 | | | | | 15 | | |

| acc | acg | cac | ggg | aag | atc | cgg | atc | cac | gac | tac | gtc | ggc | gat | ggt | tgg | 96 |
|---|---|---|---|---|---|---|---|---|---|---|---|---|---|---|---|---|
| Thr | Thr | His | Gly | Lys | Ile | Arg | Ile | His | Asp | Tyr | Val | Gly | Asp | Gly | Trp | |
| | | | 20 | | | | | 25 | | | | | 30 | | | |

| gcc | atc | atc | ttc | tcc | cat | ccc | gcg | gat | ttc | aca | ccc | gtg | tgc | acg | acg | 144 |
|---|---|---|---|---|---|---|---|---|---|---|---|---|---|---|---|---|
| Ala | Ile | Ile | Phe | Ser | His | Pro | Ala | Asp | Phe | Thr | Pro | Val | Cys | Thr | Thr | |
| | | 35 | | | | | 40 | | | | | 45 | | | | |

| gag | ctg | ggg | aag | atg | gcg | gcg | tac | gcg | gag | gag | ttc | gag | aaa | aga | ggg | 192 |
|---|---|---|---|---|---|---|---|---|---|---|---|---|---|---|---|---|
| Glu | Leu | Gly | Lys | Met | Ala | Ala | Tyr | Ala | Glu | Glu | Phe | Glu | Lys | Arg | Gly | |
| 50 | | | | | 55 | | | | | 60 | | | | | | |

| gtg | aag | ctg | cta | ggc | atc | tcc | tgc | gac | gat | gtc | aag | tgc | cac | atg | gaa | 240 |
|---|---|---|---|---|---|---|---|---|---|---|---|---|---|---|---|---|
| Val | Lys | Leu | Leu | Gly | Ile | Ser | Cys | Asp | Asp | Val | Lys | Cys | His | Met | Glu | |
| 65 | | | | | 70 | | | | | 75 | | | | | 80 | |

| tgg | atc | aaa | gac | gtc | gag | gcc | tac | acg | ccc | gga | tgt | cgc | gta | aca | tat | 288 |
|---|---|---|---|---|---|---|---|---|---|---|---|---|---|---|---|---|
| Trp | Ile | Lys | Asp | Val | Glu | Ala | Tyr | Thr | Pro | Gly | Cys | Arg | Val | Thr | Tyr | |
| | | | | 85 | | | | | 90 | | | | | 95 | | |

| cca | att | gta | gcc | gac | ccc | aag | agg | gag | gtg | atc | aaa | ctg | ctg | aac | atg | 336 |
|---|---|---|---|---|---|---|---|---|---|---|---|---|---|---|---|---|
| Pro | Ile | Val | Ala | Asp | Pro | Lys | Arg | Glu | Val | Ile | Lys | Leu | Leu | Asn | Met | |
| | | | 100 | | | | | 105 | | | | | 110 | | | |

| gta | gac | cct | gag | gag | aag | gac | tca | aat | ggg | aac | cag | ctc | ccg | tca | cgg | 384 |
|---|---|---|---|---|---|---|---|---|---|---|---|---|---|---|---|---|
| Val | Asp | Pro | Glu | Glu | Lys | Asp | Ser | Asn | Gly | Asn | Gln | Leu | Pro | Ser | Arg | |
| | | 115 | | | | | 120 | | | | | 125 | | | | |

| gcc | ctt | cat | ata | gtg | ggc | cct | gat | aag | aag | gtt | aag | ctg | agc | ttt | ctg | 432 |
|---|---|---|---|---|---|---|---|---|---|---|---|---|---|---|---|---|
| Ala | Leu | His | Ile | Val | Gly | Pro | Asp | Lys | Lys | Val | Lys | Leu | Ser | Phe | Leu | |
| | 130 | | | | | 135 | | | | | 140 | | | | | |

| tac | ccg | gcg | tcg | acg | ggg | cgg | aac | atg | gag | gag | gtg | gtc | agg | gtg | ttg | 480 |
|---|---|---|---|---|---|---|---|---|---|---|---|---|---|---|---|---|
| Tyr | Pro | Ala | Ser | Thr | Gly | Arg | Asn | Met | Glu | Glu | Val | Val | Arg | Val | Leu | |
| 145 | | | | | 150 | | | | | 155 | | | | | 160 | |

| gag | tcg | ctt | cag | aag | acg | atc | aag | tat | aag | gtg | gcg | acc | cca | gcg | aac | 528 |
|---|---|---|---|---|---|---|---|---|---|---|---|---|---|---|---|---|
| Glu | Ser | Leu | Gln | Lys | Thr | Ile | Lys | Tyr | Lys | Val | Ala | Thr | Pro | Ala | Asn | |
| | | | | 165 | | | | | 170 | | | | | 175 | | |

| tgg | aaa | ccg | ggg | gag | ccg | gtg | gtg | atc | tcg | ccc | gag | cgt | gtc | caa | | 573 |
|---|---|---|---|---|---|---|---|---|---|---|---|---|---|---|---|---|
| Trp | Lys | Pro | Gly | Glu | Pro | Val | Val | Ile | Ser | Pro | Glu | Arg | Val | Gln | | |
| | | | 180 | | | | | 185 | | | | | 190 | | | |

<210> SEQ ID NO 2
<211> LENGTH: 191
<212> TYPE: PRT
<213> ORGANISM: oil palm

<400> SEQUENCE: 2

Met Pro Gly Leu Thr Ile Gly Asp Thr Ile Pro Asn Leu Glu Val Glu
1               5                   10                  15

Thr Thr His Gly Lys Ile Arg Ile His Asp Tyr Val Gly Asp Gly Trp
            20                  25                  30

Ala Ile Ile Phe Ser His Pro Ala Asp Phe Thr Pro Val Cys Thr Thr
        35                  40                  45

```
Glu Leu Gly Lys Met Ala Ala Tyr Ala Glu Glu Phe Glu Lys Arg Gly
         50                  55                  60

Val Lys Leu Leu Gly Ile Ser Cys Asp Asp Val Lys Cys His Met Glu
 65                  70                  75                  80

Trp Ile Lys Asp Val Glu Ala Tyr Thr Pro Gly Cys Arg Val Thr Tyr
                 85                  90                  95

Pro Ile Val Ala Asp Pro Lys Arg Glu Val Ile Lys Leu Leu Asn Met
             100                 105                 110

Val Asp Pro Glu Glu Lys Asp Ser Asn Gly Asn Gln Leu Pro Ser Arg
         115                 120                 125

Ala Leu His Ile Val Gly Pro Asp Lys Lys Val Lys Leu Ser Phe Leu
     130                 135                 140

Tyr Pro Ala Ser Thr Gly Arg Asn Met Glu Val Val Arg Val Leu
145                 150                 155                 160

Glu Ser Leu Gln Lys Thr Ile Lys Tyr Lys Val Ala Thr Pro Ala Asn
                 165                 170                 175

Trp Lys Pro Gly Glu Pro Val Val Ile Ser Pro Glu Arg Val Gln
             180                 185                 190

<210> SEQ ID NO 3
<211> LENGTH: 873
<212> TYPE: DNA
<213> ORGANISM: oil palm
<220> FEATURE:
<221> NAME/KEY: CDS
<222> LOCATION: (28)..(600)

<400> SEQUENCE: 3
cacgaggtga atcggagccg ttgaaag atg ccg ggg cta acg atc ggc gac acg      54
                              Met Pro Gly Leu Thr Ile Gly Asp Thr
                                1               5 atc ccg aac ctg gag gtg gag acc acg cac ggg aag atc cgg atc cac      102
Ile Pro Asn Leu Glu Val Glu Thr Thr His Gly Lys Ile Arg Ile His
 10                  15                  20                  25 gac tac gtc ggc gat ggt tgg gcc atc atc ttc tcc cat ccc gcg gat      150
Asp Tyr Val Gly Asp Gly Trp Ala Ile Ile Phe Ser His Pro Ala Asp
                 30                  35                  40 ttc aca ccc gtg tgc acg acg gag ctg ggg aag atg gcg gcg tac gcg      198
Phe Thr Pro Val Cys Thr Thr Glu Leu Gly Lys Met Ala Ala Tyr Ala
             45                  50                  55 gag gag ttc gag aaa aga ggg gtg aag ctg cta ggc atc tcc tgc gac      246
Glu Glu Phe Glu Lys Arg Gly Val Lys Leu Leu Gly Ile Ser Cys Asp
         60                  65                  70 gat gtc aag tgc cac atg gaa tgg atc aaa gac gtc gag gcc tac acg      294
Asp Val Lys Cys His Met Glu Trp Ile Lys Asp Val Glu Ala Tyr Thr
 75                  80                  85 ccc gga tgt cgc gta aca tat cca att gta gcc gac ccc aag agg gag      342
Pro Gly Cys Arg Val Thr Tyr Pro Ile Val Ala Asp Pro Lys Arg Glu
 90                  95                 100                 105 gtg atc aaa ctg ctg aac atg gta gac cct gag gag aag gac tca aat      390
Val Ile Lys Leu Leu Asn Met Val Asp Pro Glu Glu Lys Asp Ser Asn
                 110                 115                 120 ggg aac cag ctc ccg tca cgg gcc ctt cat ata gtg ggc cct gat aag      438
Gly Asn Gln Leu Pro Ser Arg Ala Leu His Ile Val Gly Pro Asp Lys
             125                 130                 135 aag gtt aag ctg agc ttt ctg tac ccg gcg tcg acg ggg cgg aac atg      486
Lys Val Lys Leu Ser Phe Leu Tyr Pro Ala Ser Thr Gly Arg Asn Met
         140                 145                 150
```

-continued

```
gag gag gtg gtc agg gtg ttg gag tcg ctt cag aag acg atc aag tat      534
Glu Glu Val Val Arg Val Leu Glu Ser Leu Gln Lys Thr Ile Lys Tyr
    155                 160                 165 aag gtg gcg acc cca gcg aac tgg aaa ccg ggg gag ccg gtg gtg atc      582
Lys Val Ala Thr Pro Ala Asn Trp Lys Pro Gly Glu Pro Val Val Ile
170                 175                 180                 185 tcg ccc gag cgt gtc caa tgaggaggcc aagcagatgt tcccgcaggg              630
Ser Pro Glu Arg Val Gln
                190 agttgagaat gtgaatctcc catcgaagaa ggattacctc cgcttcacaa aagtctaatg     690 ttgttgggcc gtccgtgata tgttcataag tggtttctgg ggcccgactg tatactgtgt     750 tgtcgtgtta tatgtttgtg ttggtatcat gtagtttgtg ccttagggga gtttggatat     810 taatttgtag tttatgttaa ttattaaagt ttttaccatg agattaaaaa aaaaaaaaaa     870 aaa                                                                  873
```

<210> SEQ ID NO 4
<211> LENGTH: 191
<212> TYPE: PRT
<213> ORGANISM: oil palm

<400> SEQUENCE: 4

```
Met Pro Gly Leu Thr Ile Gly Asp Thr Ile Pro Asn Leu Glu Val Glu
1               5                   10                  15

Thr Thr His Gly Lys Ile Arg Ile His Asp Tyr Val Gly Asp Gly Trp
            20                  25                  30

Ala Ile Ile Phe Ser His Pro Ala Asp Phe Thr Pro Val Cys Thr Thr
        35                  40                  45

Glu Leu Gly Lys Met Ala Ala Tyr Ala Glu Glu Phe Glu Lys Arg Gly
    50                  55                  60

Val Lys Leu Leu Gly Ile Ser Cys Asp Asp Val Lys Cys His Met Glu
65                  70                  75                  80

Trp Ile Lys Asp Val Glu Ala Tyr Thr Pro Gly Cys Arg Val Thr Tyr
                85                  90                  95

Pro Ile Val Ala Asp Pro Lys Arg Glu Val Ile Lys Leu Leu Asn Met
            100                 105                 110

Val Asp Pro Glu Glu Lys Asp Ser Asn Gly Asn Gln Leu Pro Ser Arg
        115                 120                 125

Ala Leu His Ile Val Gly Pro Asp Lys Lys Val Lys Leu Ser Phe Leu
    130                 135                 140

Tyr Pro Ala Ser Thr Gly Arg Asn Met Glu Glu Val Val Arg Val Leu
145                 150                 155                 160

Glu Ser Leu Gln Lys Thr Ile Lys Tyr Lys Val Ala Thr Pro Ala Asn
                165                 170                 175

Trp Lys Pro Gly Glu Pro Val Val Ile Ser Pro Glu Arg Val Gln
            180                 185                 190
```

<210> SEQ ID NO 5
<211> LENGTH: 17
<212> TYPE: DNA
<213> ORGANISM: oil palm

<400> SEQUENCE: 5
aggaggattg tgcagag                                                    17

<210> SEQ ID NO 6
<211> LENGTH: 18

```
<212> TYPE: DNA
<213> ORGANISM: oil palm

<400> SEQUENCE: 6
caaactctca gctaggca                                                  18

<210> SEQ ID NO 7
<211> LENGTH: 218
<212> TYPE: PRT
<213> ORGANISM: Hordeum vulgare

<400> SEQUENCE: 7

Met Pro Gly Leu Thr Ile Gly Asp Thr Val Pro Asn Leu Glu Leu Asp
  1               5                  10                  15

Ser Thr His Gly Lys Ile Arg Ile His Asp Tyr Val Gly Asn Gly Tyr
             20                  25                  30

Val Ile Leu Phe Ser His Pro Gly Asp Phe Thr Pro Val Cys Thr Thr
         35                  40                  45

Glu Leu Ala Ala Met Ala Asn Tyr Ala Lys Glu Phe Glu Lys Arg Gly
     50                  55                  60

Val Lys Leu Leu Gly Ile Ser Cys Asp Val Gln Ser His Lys Glu
 65                  70                  75                  80

Trp Thr Lys Asp Ile Glu Ala Tyr Lys Pro Gly Ser Lys Val Thr Tyr
                 85                  90                  95

Pro Ile Met Ala Asp Pro Asp Arg Ser Ala Ile Lys Gln Leu Asn Met
            100                 105                 110

Val Asp Pro Asp Glu Lys Asp Ala Gln Gly Gln Leu Pro Ser Arg Thr
        115                 120                 125

Leu His Ile Val Gly Pro Asp Lys Val Val Lys Leu Ser Phe Leu Tyr
    130                 135                 140

Pro Ser Cys Thr Gly Arg Asn Met Asp Glu Val Val Arg Ala Val Asp
145                 150                 155                 160

Ser Leu Leu Thr Ala Ala Lys His Lys Val Ala Thr Pro Ala Asn Trp
                165                 170                 175

Lys Pro Gly Glu Cys Val Val Ile Ala Pro Gly Val Ser Asp Glu Glu
            180                 185                 190

Ala Lys Lys Met Phe Pro Gln Gly Phe Glu Thr Ala Asp Leu Pro Ser
        195                 200                 205

Lys Lys Gly Tyr Leu Arg Phe Thr Lys Val
    210                 215

<210> SEQ ID NO 8
<211> LENGTH: 216
<212> TYPE: PRT
<213> ORGANISM: Arabidopsis thaliana

<400> SEQUENCE: 8

Met Pro Gly Ile Thr Leu Gly Asp Thr Val Pro Asn Leu Glu Val Glu
  1               5                  10                  15

Thr Thr His Asp Lys Phe Lys Leu His Asp Tyr Phe Ala Asn Ser Trp
             20                  25                  30

Thr Val Leu Phe Ser His Pro Gly Asp Phe Thr Pro Val Cys Thr Thr
         35                  40                  45

Glu Leu Gly Ala Met Ala Lys Tyr Ala His Glu Phe Asp Lys Arg Gly
     50                  55                  60

Val Lys Leu Leu Gly Leu Ser Cys Asp Val Gln Ser His Lys Asp
 65                  70                  75                  80
```

```
Trp Ile Lys Asp Ile Glu Ala Phe Asn His Gly Ser Lys Val Asn Tyr
                85                  90                  95

Pro Ile Ile Ala Asp Pro Asn Lys Glu Ile Ile Pro Gln Leu Asn Met
            100                 105                 110

Ile Asp Pro Ile Glu Asn Gly Pro Ser Arg Ala Leu His Ile Val Gly
        115                 120                 125

Pro Asp Ser Lys Ile Lys Leu Ser Phe Leu Tyr Pro Ser Thr Thr Gly
    130                 135                 140

Arg Asn Met Asp Glu Val Leu Arg Ala Leu Asp Ser Leu Leu Met Ala
145                 150                 155                 160

Ser Lys His Asn Asn Lys Ile Ala Thr Pro Val Asn Trp Lys Pro Asp
                165                 170                 175

Gln Pro Val Val Ile Ser Pro Ala Val Ser Asp Glu Ala Lys Lys
            180                 185                 190

Met Phe Pro Gln Gly Phe Lys Thr Ala Asp Leu Pro Ser Lys Lys Gly
        195                 200                 205

Tyr Leu Arg His Thr Glu Val Ser
    210                 215

<210> SEQ ID NO 9
<211> LENGTH: 272
<212> TYPE: PRT
<213> ORGANISM: Brassica campestri

<400> SEQUENCE: 9

Met Ala Ser Val Ala Ser Ser Thr Thr Leu Ile Ser Ser Ser Ala Ser
1               5                   10                  15

Val Leu Pro Ala Thr Lys Ser Ser Leu Leu Pro Ser Pro Ser Leu Ser
            20                  25                  30

Phe Leu Pro Thr Leu Ser Ser Pro Ser Pro Ser Ala Ser Leu Arg Ser
        35                  40                  45

Leu Val Pro Leu Pro Ser Pro Gln Ser Ala Ser Ser Arg Arg Ser
    50                  55                  60

Phe Ala Val Lys Gly Gln Thr Asp Asp Leu Pro Leu Val Gly Asn Lys
65                  70                  75                  80

Ala Pro Asp Phe Glu Ala Glu Gly Val Phe Asp Gln Glu Phe Ile Lys
                85                  90                  95

Phe Ile Lys Val Lys Leu Ser Asp Tyr Ile Gly Lys Lys Tyr Val Ile
            100                 105                 110

Leu Phe Phe Leu Pro Leu Asp Phe Thr Phe Val Cys Pro Thr Glu Ile
        115                 120                 125

Thr Ala Phe Ser Asp Arg Tyr Ala Glu Phe Glu Lys Leu Asn Thr Glu
    130                 135                 140

Val Leu Gly Val Ser Val Asp Ser Val Ser Val Phe Ser His Leu Ala
145                 150                 155                 160

Gly Val Gln Thr Asp Arg Lys Phe Gly Gly Leu Gly Asp Leu Asn Tyr
                165                 170                 175

Pro Leu Ile Ser Asp Val Thr Lys Ser Ile Ser Lys Ser Phe Gly Val
            180                 185                 190

Leu Ile His Asp Gln Gly Ile Ala Leu Arg Gly Leu Phe Ile Ile Asp
        195                 200                 205

Lys Glu Gly Val Ile Gln His Ser Thr Ile Asn Leu Gly Ile Gly Arg
    210                 215                 220

Ser Val Asp Glu Thr Met Arg Thr Leu Gln Ala Leu Gln Tyr Ile Gln
```

```
                                      -continued
225                 230                 235                 240
Glu Gly Pro Gly Glu Val Cys Pro Ala Gly Trp Lys Pro Gly Glu Lys
                245                 250                 255

Ser Met Lys Pro Asp Pro Lys Leu Ser Lys Glu Leu Phe Ser Ala Ile
            260                 265                 270
```

MOLECULAR MARKERS OF PLANT EMBRYOGENESIS

FIELD OF THE INVENTION

The present invention relates generally to a molecular marker for a plant physiological process and more particularly for plant embryogenesis. The molecular marker is, in one form, a genetic sequence from a monocot plant such as but not limited to oil-palm plants. In another form, the molecular marker is a polypeptide encoded by said genetic sequence. More particularly, the molecular marker of the present invention enables embryogenic tissue to be detected in vitro. The early detection of embryogenic tissue enables non-embryogenic tissue to be discarded. The ability to detect embryogenesis facilitates maximization of embryogenic potential. The present invention further contemplates a molecular marker comprising in one form a sequence of nucleotides encoding an antioxidant or in another form a sequence of amino acids defining a polypeptide having antioxidant activity. The antioxidant according to this aspect of the present invention is particularly useful in tablet or cream form as an anti-aging agent. The molecular markers of the present invention therefore also have uses in the inhibition or retardation of apoptotic processes. Such an effect has benefits in both plant and animal cells. The present invention further contemplates a promoter sequence encoding the molecular marker and its use in generating male sterile plants.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in Australia or any other country.

The study of plant embryogenesis has been regarded as fundamental to understanding plant development. It is during embryogenesis that meristems and basic plant tissue systems are established. Basically, embryogenesis involves two main processes: the induction of embryogenic potential and the expression of the embryogenesis programme. Because of the totipotency of the plant cells, each cell has the capability to become embryogenic and to develop into a whole plant.

Recent advances in micropropagation and manipulation of tissue culture conditions has led to the possibility of multiplying vegetatively many plant species efficiently and rapidly in vitro. For many commercial production systems, conventional plant breeding and seed production methods are slow and therefore limit the ability to realize the maximum potential of selected genotypes. However, the development of economically-viable propagation systems necessitates the existence of efficient methods of embryo- or organogenesis. Such methods have been generated for many, but not all species.

There are very high demands for oil-palm. Accordingly, a major area of study in the oil-palm industry seeks to find improved ways to increase oil yield. With the ability to maintain uniformity of planting materials in tissue culture, improvements in yield of up to 20% may be able to be realized. In the case of oil-palm, however, little is known about the biology of somatic embryogenesis despite the economic importance of the crop and work to date has resulted in average rates of in vitro embryogenesis of only 6% (Wooi, 1995). Such low rates are inconsistent with an economically viable system.

Most of the earlier studies concentrated on the development of methodologies for the initiation and production of somatic embryos (Jones, 1974; Ahee et al., 1981; Pannetier et al., 1981). These groups worked mainly on the manipulation of phytohormones in the media as well as on introducing tissues with better clonability to further improve the process. Schwendiman and colleagues (1988) carried out histological analysis of somatic embryogenesis from leaf-derived callus, detailing the emergence of callus and the subsequent formation of somatic embryos, with shoot and root apices. Not long before that, Turnham and Northcote (1982) investigated the occurrence of biochemical indicators that are useful in the prediction of embryogenic potential.

More recently, the importance of understanding molecular switches, that occur in somatic cells and induce them to become embryogenic, has been highlighted (Dudits et al., 1995).

In this regard, the rapid introduction of and improvements in recombinant DNA technologies has greatly facilitated the study of plant development and provided researchers with sophisticated precision tools for investigating underlying molecular mechanisms.

There is a need to develop an effective and efficient method for the production of somatic embryos and new approaches to be brought to bear in attempts to realize that end.

In work leading up to the present invention, the inventors sought to identify underlying factors involved in the induction of embryogenesis. In so doing the inventors located and isolated a polynucleotide sequence which was surprisingly found to be expressed only in zygotic embryo and embryogenic callus. The polynucleotide sequence or an amino acid encoded thereby of the present invention is useful inter alia as a means of discriminating embryogenic from non-embryogenic material. The molecular marker represents a member of a new class of molecules from monocot plants such as but not limited to oil-palm and related plants.

SUMMARY OF THE INVENTION

Throughout this specification, unless the context requires otherwise, the words "comprise", "comprises" and "comprising" will be understood to imply the inclusion of a stated step or element or group of steps or elements but not the exclusion of any other step or element or group of steps or elements.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The present invention provides a developmentally-regulated nucleic acid molecule designated herein as OPEm1. The nucleic acid molecule comprises a nucleotide coding sequence substantially as set forth in SEQ ID NO:1. Additional 3' and 5' sequences are provided in SEQ ID NO:3. The nucleic acid molecule is expressed only in zygotic embryo and embryonic callus to produce a polypeptide comprising the amino acid sequence set forth in SEQ ID NO:2 (corresponding to SEQ ID NO:1) or SEQ ID NO:4 (corresponding to SEQ ID NO:3). The identification of the nucleic acid molecule permits the discrimination of plant tissue at different developmental stages. The nucleic acid molecule, therefore, permits identification of a plant physiological process or tissue or other plant material associated with a plant physiological process.

The nucleic acid molecule and/or the polypeptide encoded thereby of the present invention may be used as a means of discriminating embryogenic from non-embryogenic material in plants, in particular monocot plants and even more particularly in oil-palm and related plants. The present invention provides a nucleic acid molecule, recombinant and purified naturally-occurring polypeptides, antibodies to the polypeptides as well as transgenic and genetically-modified plants. Furthermore, the polypeptides of the present invention also have anti-apoptotic properties, making them useful in the preparation of pharmaceutical compositions for use as anti-ageing agents.

Accordingly, one aspect of the present invention provides an isolated nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

Another aspect of the present invention provides an isolated nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

A further aspect of the present invention provides an isolated nucleic acid molecule capable of discriminating embryogenic from non-embryogenic material, wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

Yet another aspect of the present invention provides an isolated nucleic acid molecule comprising a polynucleotide sequence substantially as set forth in SEQ ID NO:1 or SEQ ID NO:3.

Still another aspect of the present invention provides a genetic construct comprising a nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

Even still another aspect of the present invention provides a genetic construct comprising a nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

Even yet another aspect of the present invention provides a vector comprising a nucleic acid molecule capable of discriminating embryogenic from non-embryogenic material, wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or a nucleotide sequence capable of hybridizing to SEQ ID NO:1 or SEQ ID NO:3 or its complementary form under low stringency conditions.

Another aspect of the instant invention provides a host cell comprising nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

A further aspect of the present invention provides an isolated polypeptide or biologically-active fragment thereof or a variant or derivative of these, said polypeptide comprising the amino acid sequence set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

Yet another aspect of the present invention is directed to an isolated polypeptide comprising a sequence of amino acids encoded by the nucleotide sequence substantially as set forth in SEQ ID NO:1 or SEQ ID NO:3 or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

Still another aspect of the present invention provides a method for producing a recombinant polypeptide in a host cell or tissue, said method comprising introducing into the said cell or tissue an expression vector comprising a nucleic acid molecule wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions wherein said nucleic acid molecule is operably linked to one or more regulatory sequences such that the nucleic acid molecule is capable of being expressed in said cell or tissue.

Even still another aspect of the invention provides a method for modulating apoptotic processes in a cell or tissue, said method comprising introducing into said cell or tissue an expression vector comprising a nucleic acid molecule, said nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions wherein said nucleic acid molecule is operably linked to one or more regulatory sequences such that the nucleic acid molecule is capable of being expressed in said cell or tissue.

Even yet another aspect of the invention provides a method for modulating apoptotic processes in a cell, said method comprising administering to said cell an apoptotic process-controlling effective amount of a recombinant polypeptide, said polypeptide comprising the amino acid sequence set forth in SEQ ID NO:2 or an amino acid sequence having at least about 71% similarity to SEQ ID NO:2, said administration being for a time and under conditions sufficient to modulate apoptosis.

Another aspect of the invention provides a method for detecting embryogenic plant material, said method comprising immobilizing a sample putatively containing RNA from the material to be screened on a solid support and contacting said immobilized RNA with a labelled nucleotide sequence capable of hybridizing to all or part of an mRNA transcript corresponding to the nucleotide sequence set forth in SEQ ID NO:1 or SEQ ID NO:3 or their derivatives or homologues as defined herein and then detecting the presence of said label.

A further aspect of the present invention contemplates an antibody to a polypeptide, said polypeptide comprising a sequence of amino acids substantially as set forth in SEQ ID NO:2 or an amino acid sequence having at least 71% similarity to SEQ ID NO:2, wherein said polypeptide is present in plant zygotic embryos or embryogenic callus and is substantially not present in non-embryogenic tissue.

Yet another aspect of the present invention contemplates a method for detecting a polypeptide which is indicative of the presence of embryogenic tissue in oil-palm or related plants, said method comprising contacting the tissue or an extract thereof with an antibody specific for said polypeptide or its derivatives or homologues for a time and under conditions sufficient for an antibody-polypeptide complex to form, and then detecting said complex.

Still another aspect of the present invention contemplates a pharmaceutical composition comprising the polypeptide having an amino acid sequence as set forth in SEQ ID NO:2 or a functional homologue thereof or a molecule having at least 71% similarity to SEQ ID NO:2 and one or more pharmaceutically-acceptable carriers and/or diluents.

Even still another aspect of the present invention is directed to a regenerated differentiated plant comprising a nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

Even yet another aspect of the present invention is directed to a regenerated differentiated plant comprising a nucleic acid molecule, wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

Another aspect of the present invention provides an isolated nucleic acid molecule having promoter activity wherein, in its naturally occurring form, the promoter is operably linked to a nucleotide sequence substantially as set forth in SEQ ID NO:1 or SEQ ID NO:3 or a nucleotide sequence complementary thereto or a nucleotide sequence capable of hybridizing to SEQ ID NO:1 or SEQ ID NO:3 or its complementary form under low stringency conditions.

SUMMARY OF SEQUENCE IDENTIFIERS

| SEQUENCE IDENTIFIER | DESCRIPTION |
| --- | --- |
| SEQ ID NO: 1 | Nucleotide coding sequence of embryogenic specific polypeptide from oil-palm (OPEm1) |
| SEQ ID NO: 2 | Amino acid sequence of embryogenic specific polypeptide from oil-palm (OPEm1); corresponds to SEQ ID NO: 1 |
| SEQ ID NO: 3 | Nucleotide coding sequence of embryogenic specific polypeptide from oil-palm (OPEm1) with 5' and 3' non-transcribed sequences |
| SEQ ID NO: 4 | Amino acid sequence of embryogenic specific polypeptide from oil-palm (OPEm1); corresponds to SEQ ID NO: 3 |
| SEQ ID NO: 5 | Oligonucleotide primer AGL15AtF |
| SEQ ID NO: 6 | Oligonucleotide primer AGL15AtR |

-continued

| SEQUENCE IDENTIFIER | DESCRIPTION |
| --- | --- |
| SEQ ID NO: 7 | Amino acid sequence of 1-Cys peroxiredoxin from *Hordeum vulgare* (barley) [HvPer1] |
| SEQ ID NO: 8 | Amino acid sequence of 1-Cys peroxiredoxin from *Arabidopsis thaliana* (thalecress) [AtPer1] |
| SEQ ID NO: 9 | Amino acid sequence of 1-Cys peroxiredoxin from *Brassica campestris* (Chinese cabbage) [C2CPRX] |

BRIEF DESCRIPTION OF THE FIGURES

FIG. 3 is the nucleotide (SEQ ID NO: 3) and deduced amino acid (SEQ ID NO: 2) sequences of OPEm1.

FIG. 5 is the sequence alignment of OPEm1 (SEQ ID NO: 2) with examples of 1-Cys and 2-Cys peroxiredoxins. The '*' denotes a single fully conserved residue. The ':' denotes conservation of strong groups. The '.' conservation of weak groups. Those without any symbol denote no consensus (CLUSTALW), Biology Workbench Version 3.2, University of Illinois, 1999). The amino acid sequences were obtained from Genbank: HvPer1 (*Hordeum vulgare*, barley, P52572) (SEQ ID NO: 7), AtPer1 (*Arabidopsis thaliana*, thalecress, CAA63909) (SEQ ID NO: 8) and C2CPRX (*Brassica campestris* L. ssp. *pekinensis*, chinese cabbage) (SEQ ID NO: 9.

Figure 1A:
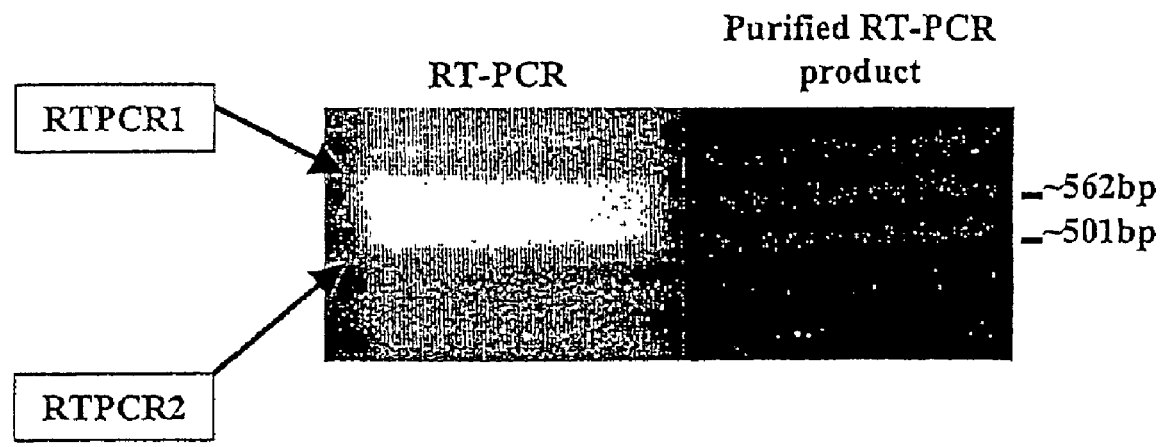
FIG. 1a is a photographic representation showing reverse transcription of zygotic embryo total RNA with primers AGL15AtF and AGL15AtR resulting in the production of two bands, designated RTPCR1 (~562 bp) and RTPCR2 (~501 bp) (left). The bands were excised and purified (right).

FIG. 6 is the sequence alignment of OPEm1 (SEQ ID NO: 2) with examples of other members of 1-Cys peroxiredoxin. The '*' denotes a single fully conserved residue. The ':' denotes conservation of strong groups. The '.' denotes conservation of weak groups. Those without any symbols denote no consensus. (CLUSTALW, Biology Workbench Version 3.2, University of Illinois, 1999). The peroxiredoxin amino acid sequences were obtained from Genebank: HvPer1 (*Hordeum vulgare*, barley, P52572) (SEQ ID NO: 7) and AtPer1 (*Arabidopsis thaliana*, thalecress, CAA63909) (SEQ ID NO: 8). The '#' and '@' denote the positively charged residue His 38 and Arg 128 respectively, which are all found close to the Cys 46. The PVCT region represents a specific characteristic of the 1-Cys peroxiredoxin. The basis residues at the terminal end of the 1-Cys peroxiredoxin align to the nuclear localization signal (NLS) region that is not present in OPEm1. A coloured version of this Figure where the PVCT region is in blue and the basic region is in red is available from the Applicant upon request.

DETAILED DESCRIPTION OF THE PREFERRED EMBODIMENTS

The present invention is predicated in part on the identification of a developmentally-regulated nucleic acid molecule. The identification of the nucleic acid molecule permits the discrimination of plant tissue at different developmental stages. The nucleic acid molecule, therefore, permits identification of a plant physiological process or tissue or other plant material associated with a plant physiological process. More particularly, the polynucleotide sequence is expressed only in zygotic embryo and embryogenic callus. The nucleic acid molecule and/or an amino acid sequence encoded thereby of the present invention may be used as a means of discriminating embryogenic from non-embryogenic material in plants, in particular monocot plants and even more particularly in oil-palm and related plants. The term "material" includes cells, tissue, clusters of cells, callus, organelles, seeds, pollen and other plant parts. The nucleic acid molecule of the present invention and an amino acid sequence encoded thereby are both referred to herein as a "molecular marker". Reference herein to a "molecular marker" is not to impart any limitation as to its structure, location in a cell or its use.

Reference to the term "discriminating" in relation to embryogenic and non-embryogenic tissue includes reference to the determination of a strong likelihood that certain tissue is embryogenic as distinct from non-embryogenic on the basis of the presence of the subject nucleic acid molecule or its expression product. Reference to a "determination" includes reference to a "prediction" or other reasoned deduction. Embryogenic material includes inter alia zygotic embryo and embryogenic callus material.

Accordingly, one aspect of the present invention provides an isolated nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

In a related embodiment, the present invention provides an isolated nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

Preferably the nucleic acid molecule is regulated developmentally such that its presence may be used as a means of discriminating embryogenic from non-embryogenic material.

Accordingly, in a preferred embodiment, the present invention provides an isolated nucleic acid molecule capable of discriminating embryogenic from non-embryogenic material, wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

The term "nucleic acid molecule" includes a polynucleotide, nucleotide or genetic sequence such as, but not limited to, mRNA, RNA, cRNA, cDNA or DNA. Reference to a DNA molecule includes genomic DNA.

By "isolated" is meant material that is substantially or essentially free from components that normally accompany it in its native state. For example, an "isolated nucleic acid molecule" as used herein refers to a polynucleotide sequence, which has been purified from the sequences which flank it in a naturally-occurring state, e.g., a DNA fragment which has been removed from the sequences which are normally adjacent to the fragment.

The isolated nucleotide sequence of the present invention also extends to derivatives including, mutants and homologues of the said sequence.

By "derivative" is meant any single or multiple nucleotide deletions, additions or substitutions as well as mutants, fragments, portions or parts of said isolated nucleic acid molecule. All such deletions, additions, substitutions, mutants, fragments, portions, or parts are encompassed by the term "derivative". Particularly useful derivatives include alterations to the 5' end portion of the polynucleotide sequence or the 3' end portion or a nucleotide sequence spanning the 5' and 3' portions. Synthetic derivatives may also be useful, for example, in diagnostic assays. A derivative also conveniently includes a polynucleotide sequence having less than 100% identity with the nucleotide sequence set forth in SEQ ID NO:1, but which is capable of hybridizing thereto or its complementary form under low stringency conditions.

Terms such as "hybridization", "hybridizing" and the like are used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

"Stringency" as used herein, refers to the temperature and ionic strength conditions, and presence or absence of certain organic solvents, during hybridization and washing procedures. The higher the stringency, the higher will be the degree of complementarity between immobilized target nucleotide sequences and the labelled probe polynucleotide sequences that remain hybridized to the target after washing.

"Stringency conditions" refers to temperature and ionic conditions under which only nucleotide sequences having a high frequency of complementary bases will hybridize. The stringency required is nucleotide sequence dependent and depends upon the various components present during hybridization and subsequent washes, and the time allowed for these processes. Generally, in order to maximize the hybridization rate, non-stringent hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 71% nucleotide complementarity of hybridized sequences, moderately stringent washing conditions are selected to be about 15 to 30° C. lower than the $T_m$. Highly permissive (low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, 1962). However, the $T_m$ of a duplex DNA decreases by 1° C. with every increase of 1% in the number of mismatch base pairs (Bonner and Laskey, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Suitably, the isolated nucleic acid molecule has at least greater than 70% (for example, 71%), preferably at least about 75%, more preferably at least about 80%, more preferably yet at least about 85%, still more preferably at least about 90% and even still more preferably at least about 95% or above (e.g. 96% or 97% or 98% or 99%) sequence similarity to the nucleotide sequence set forth in SEQ ID NO:1 or SEQ ID NO:3.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997). A detailed discussion of sequence analysis can be found in Unit 19.3 of Ausubel et al. (1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

A particularly preferred embodiment of the instant invention provides an isolated nucleic acid molecule comprising a polynucleotide sequence substantially as set forth in SEQ ID NO:1 or SEQ ID NO:3. Although the present invention is particularly exemplified with respect to oil-palm, this is done with the understanding that the instant invention encompasses any monocot plant. Reference herein to a monocot includes any member of the plant family Gramineae, Palmae, Juncaceae and Achenes, but is not limited to cereals, grasses, maize, sugar cane, oats, wheat, barley as well as oil-palm.

In a convenient embodiment, reference to a nucleic acid molecule includes reference to a "gene". The term "gene" is used in its broadest sense and includes reference to a polynucleotide sequence such as a cDNA corresponding to the exons of a gene. Accordingly, reference herein to a "gene" is to be taken to include:—

(i) a classical genomic gene consisting of transcriptional and/or translational regulatory sequences and/or a coding region and/or non-translated sequences (i.e. introns, 5'- and 3'-untranslated sequences); or
(ii) mRNA or cDNA corresponding to the coding regions (i.e. exons) and 5'- and 3'-untranslated sequences of the gene; and/or
(iii) a structural region corresponding to the coding regions (i.e. exons) optionally further comprising untranslated sequences and/or a heterologous promoter sequence which consists of transcriptional and/or translational regulatory regions capable of conferring expression characteristics on said structural region.

The term "gene" is also used to describe synthetic or fusion molecules encoding all or part of a functional product, in particular, a sense or antisense mRNA product or a peptide, oligopeptide or polypeptide or a biologically-active protein. Reference to a "gene" also includes reference to a "synthetic gene".

The term "synthetic gene" refers to a non-naturally occurring gene as hereinbefore defined which preferably comprises at least one or more transcriptional and/or translational regulatory sequences operably linked to a structural gene sequence.

The term "structural gene" shall be taken to refer to a nucleotide sequence, which is capable of being transmitted to produce mRNA and optionally, encodes a peptide, oligopeptide, polypeptide or biologically active protein molecule. Those skilled in the art will be aware that not all mRNA is capable of being translated into a peptide, oligopeptide, polypeptide or protein; for example, if the mRNA lacks a functional translation start signal or alternatively, if the mRNA is antisense mRNA. The present invention clearly encompasses synthetic genes comprising nucleotide sequences, which are not capable of encoding peptides, oligopeptides, polypeptides or biologically-active proteins. In particular, the present inventors have found that such synthetic genes may be useful, for example, in diagnostic assays of gene expression in cells, tissues or organs of a eukaroytic organism.

The term "structural gene region" refers to that part of a synthetic gene, which is expressed in a cell, tissue or organ under the control of a promoter sequence to which it is operably connected. A structural gene region may be operably under the control of a single promoter sequence or multiple promoter sequences. Accordingly, the structural gene region of a synthetic gene may comprise a nucleotide sequence, which is capable of encoding an amino acid sequence or is complementary thereto. In this regard, a structural gene region, which is used in the performance of the instant invention, may also comprise a nucleotide sequence which encodes an amino acid sequence yet lacks a functional translation initiation codon and/or a functional translation stop codon and, as a consequence, does not comprise a complete open reading frame. In the present context, the term "structural gene region" also extends to a non-coding nucleotide sequences, such as 5'-upstream or 3'-downstream sequences of a gene which would not normally be translated in a eukaryotic cell which expresses said gene.

In another aspect, the invention is directed to a vector comprising the nucleic acid molecule as broadly described above. The vector comprising the nucleic acid molecule may be in isolated form or may exist as an extrachromosomal element or all or part of the vector may be integrated into the genome of a host cell. The vector may also be packaged for sale in a kit with instructions for use inter alia as a diagnostic agent or in an assay system.

In a preferred embodiment, the instant invention provides a vector comprising a nucleic acid molecule having a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

A particularly preferred embodiment of the present invention provides a vector comprising a nucleic acid molecule capable of discriminating embryogenic from non-embryogenic material, wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or a nucleotide sequence capable of hybridizing to SEQ ID NO:1 or SEQ ID NO:3 or its complementary form under low stringency conditions.

Furthermore, the vector may comprise a nucleic acid molecule which when transcribed generates a mRNA which is antisense relative to the transcript generated by SEQ ID NO:1 or SEQ ID NO:3 or its related sequence. A related sequence includes a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions. A related sequence, therefore, includes a derivative and homologue.

In a further related embodiment, the invention is directed to a vector comprising a polynucleotide sequence as broadly described above wherein the polynucleotide sequence is operably linked to one or more regulatory sequences, including but not limited to a promoter sequence and/or a transcription terminator sequence.

By "operably linked" is meant that transcriptional and translational regulatory nucleic acids are positioned relative to a functional coding region in such a manner that the functional coding region is transcribed and optionally the polypeptide is translated. The term "functional" includes a nucleotide sequence which encodes a peptide, polypeptide or protein, or which exhibits some other function such as but not limited to binding to DNA or RNA.

By "vector" is meant a nucleic acid molecule, preferably a DNA molecule derived, for example, from a plasmid, bacteriophage, or plant virus, into which a nucleic acid sequence may be inserted or cloned. A vector may also be a form of genetic construct. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e. a vector that exists as an extrachromosomal entity, the replication of which is independent of chromosomal replication, e.g. a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selectable marker such as an antibiotic resistance gene that can be used for selection of suitable transformants. Examples of such resistance genes are well known to those of skill in the art.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', or a structural gene region, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a nucleic acid molecule in a cell. The term "expression" encompasses transcription to a mRNA molecule alone or both transcription and translation to a corresponding amino acid sequence. By "mRNA" is meant either a sense or antisense mRNA molecule.

Preferred promoters may contain additional copies of one or more specific regulatory elements, to further enhance expression of the sense molecule and/or to alter the spatial expression and/or temporal expression of said sense molecule. For example, regulatory elements which confer copper inducibility may be placed adjacent to a heterologous promoter sequence driving expression of a sense molecule, thereby conferring copper inducibility on the expression of said molecules.

Placing a nucleic acid molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations, it is generally preferred to position the promoter at a distance from the gene transcription start site that is approximately the same as the distance between that promoter and the gene it controls in its natural setting, i.e. the gene from which the promoter is derived. As is known in the art, some variation in this distance can be accommodated without loss of promoter function.

Similarly, the preferred positioning of a regulatory sequence element with respect to a heterologous gene to be placed under its control is defined by the positioning of the element in its natural setting, i.e. the genes from which it is derived. Again, as is known in the art, some variation in this distance can also occur.

Examples of promoters suitable for use in the synthetic genes of the present invention include viral, fungal, bacterial, animal and plant derived promoters capable of functioning in plant, animal, insect, fungal, yeast or bacterial cells. The promoter may regulate the expression of the structural gene component constitutively, or differentially with respect to cell, the tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a eukaryotic cell, tissue or organ, at least during the period of time over which the target gene is expressed therein and more preferably also immediately preceding the commencement of detectable expression of the target gene in said cell, tissue or organ.

Accordingly, strong constitutive promoters are particularly useful for the purposes of the present invention or promoters, which may be induced by virus infection or the commencement of target gene expression.

Plant-operable and animal-operable promoters are particularly preferred for use in the construct of the present invention. Examples of preferred promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, CaMV 35S promoter, SCSV promoter, SCBV promoter and the like.

In consideration of the preferred requirement for high-level expression which coincides with expression of the target gene or precedes expression of the target gene, it is highly desirable that the promoter sequence is a constitutive strong promoter such as the CMV-IE promoter or the SV40 early promoter sequence, the SV40 late promoter sequence, the CaMV 35S promoter, or the SCBV promoter, amongst others. Those skilled in the art will readily be aware of additional promoter sequences other than those specifically described.

In the present context, the terms "in operable connection with" or "operably under the control" or similar shall be taken to indicate that expression of the structural gene region or multiple structural gene region is under the control of the promoter sequence with which it is spatially connected; in a cell, tissue, organ or whole organism.

The construct preferably contains additional regulatory elements for efficient transcription, for example, a transcription termination sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants or synthesized de novo.

As with promoter sequences, the terminator may be any terminator sequence which is operable in the cells, tissues or organs in which it is intended to be used.

The present invention further extends to the promoter of the gene sequence defined by SEQ ID NO:1 or SEQ ID NO:3. Accordingly, another aspect of the present invention contemplates an isolated nucleic acid molecule having promoter activity wherein, in its naturally occurring form, the promoter is operably linked to a nucleotide sequence substantially as set forth in SEQ ID NO:1 or SEQ ID NO:3 or a nucleotide sequence complementary thereto or a nucleotide sequence capable of hybridizing to SEQ ID NO:1 or SEQ ID NO:3 or its complementary form under low stringency conditions.

Examples of terminators particularly suitable for use in the synthetic genes of the present invention include the SV40 polyadenylation signal, the HSV TK polyadenylation signal, the CYC1 terminator, ADH terminator, SPA terminator, nopaline synthase (NOS) gene terminator of *Agrobacterium tumefaciens*, the terminator of the cauliflower mosaic virus (CaMV) 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is the SV40 polyadenylation signal or the HSV TK polyadenylation signal which are operable in animal cells, tissues and organs, octopine synthase (OCS) or nopaline synthase (NOS) terminator active in plant cells, tissue or organs, or the lacZ alpha terminator which is active in prokaryotic cells.

Those skilled in the art will be aware of additional terminator sequences, which may be suitable for use in performing the invention. Such sequences may readily be used without any undue experimentation.

Another aspect provides a host cell containing the nucleic acid molecule of the present invention. In one embodiment the said nucleic acid molecule is conveniently comprised within a vector as hereinbefore described. In another embodiment, all or part of the nucleic acid molecule of the present invention may be integrated into the DNA of the host cell. Suitably, the host cell is a bacterium or other prokaryote, or a plant cell or other eukaryote. In a particularly preferred embodiment, the plant is oil-palm or a related plant. A related plant is one which includes a plant having similarity at the genetic, biochemical, immunological, physiological or behavioural levels to oil-palm plants. Genetic similarity, for example, includes similar codon usage, genetic organization and nucleotide similarity (e.g. at least about 71% similarity over defined regions).

Accordingly, a further aspect of the instant invention provides a host cell comprising a nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

The present invention also contemplates the production of recombinant proteins, polypeptides or peptides in a host cell. A reference herein to "proteins", "polypeptides" or "peptides" is a reference to a polymer of amino acid residues and to variants of the same. The terms "proteins", "polypeptides" and "peptides" are used interchangeably. The production of recombinant polypeptides is useful, for example, to generate molecules for production of antibodies for use as a diagnostic agent or as a potential therapeutic.

Accordingly, another aspect of the present invention provides an isolated polypeptide or biologically-active fragment thereof or a variant or derivative of these, said polypeptide, comprising the amino acid sequence set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

In a related embodiment, the present invention is directed to an isolated polypeptide comprising a sequence of amino acids encoded by the nucleotide sequence substantially as set forth in SEQ ID NO:1 or SEQ ID NO:3 or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

In one embodiment, without wishing to limit the present invention to any one theory or mode of operation, the polypeptide may be useful as an antioxidant for the modulation of cellular apoptotic processes. Cell wall metabolism involves deposition of insoluble proteins that can be observed as thickening of the cell wall surrounding the proembryos. The insolubization process has been linked to the presence of hydrogen peroxide which accumulates during metabolic processes. Hence, in a particular embodiment, the nucleic acid molecule of the present invention encodes an antioxidant only found in embryogenic tissues, and which may be responsible for protecting proembryos from being destroyed by the accumulation of hydrogen peroxide within cells. In a particularly preferred embodiment, the polypeptide of the present invention encodes a peroxiredoxin useful for the modulation of cellular apoptotic processes. In another embodiment, the polypeptide is useful as an immunological agent to generate antibodies useful as diagnostic markers.

By "biologically active fragment" is meant a fragment of a full-length parent polypeptide which fragment retains the activity of the parent polypeptide. A biologically active fragment may therefore comprise peroxiredoxin activity, which protects tissues from reactive oxygen species (ROS). Alternatively, or in addition, the fragment may retain one or more epitopes for generating antibodies therefor. As used herein, the term "biologically active fragment" includes deletion mutants and small peptides, for example, of at least 10, preferably at least 20 and more preferably at least 30 contiguous amino acids, which comprise the above activities. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

Hence, another aspect of the present invention provides a method for producing a recombinant polypeptide in a host cell or tissue, said method comprising introducing into the said cell or tissue an expression vector comprising a nucleic acid molecule wherein said nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions wherein said nucleic acid molecule is operably linked to one or more regulatory sequences such that the nucleic acid molecule is capable of being expressed in said cell or tissue.

According to another aspect of the invention, there is provided a method for modulating apoptotic processes in a cell or tissue, said method comprising introducing into said cell or tissue an expression vector comprising a nucleic acid molecule, said nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions wherein said nucleic acid molecule is operably linked to one or more regulatory sequences such that the nucleic acid molecule is capable of being expressed in said cell or tissue.

In an alternative embodiment, the present invention contemplates a method for modulating apoptotic processes in a cell, said method comprising administering to said cell an apoptotic process-controlling effective amount of a recombinant polypeptide, said polypeptide comprising the amino acid sequence set forth in SEQ ID NO:2 or an amino acid sequence having at least about 71% similarity to SEQ ID NO:2, said administration being for a time and under conditions sufficient to modulate apoptosis.

The terms "modulating" and "modulate" include up-regulating and down-regulating expression of the subject nucleic acid molecule or levels of the instant polypeptide. Inducing apoptosis may be useful in the treatment of plants and animals (including humans) of cancers, galls and other outgrowths. Preventing apoptosis may be important for treating neurodegenerative disorders or other necrotic conditions. Accordingly, the present invention further contemplates a composition, such as a pharmaceutical composition, comprising the polypeptide of the instant invention or comprising genetic molecules capable of encoding said polypeptide. Such composition generally also comprises one or more pharmaceutically acceptable carriers and/or diluents.

Means of introducing vectors into cells or tissues (i.e. transfecting or transforming target cells) are well-known to those skilled in the art.

The constructs described supra are capable of being modified further, for example, by the inclusion of marker nucleotide sequences encoding a detectable marker enzyme or a functional analogue or derivative thereof, to facilitate detection of the synthetic gene in a cell, tissue or organ in which it is expressed. According to this embodiment, the marker nucleotide sequences will be present in a translatable format and expressed, for example, as a fusion polypeptide with the translation product(s) of any one or more of the structural genes or alternatively as a non-fusion polypeptide.

Those skilled in the art will be aware of how to produce the synthetic genes described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an E. coli cell or a plant cell or an animal cell.

The constructs of the present invention may be introduced to a suitable cell, tissue or organ without modification as linear DNA, optionally contained within a suitable carrier, such as a cell, virus particle or liposome, amongst others. To produce a genetic construct, the synthetic gene of the invention is inserted into a suitable vector or opisome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly, another aspect of the present invention provides a genetic construct comprising a nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

In a related aspect of the invention, there is provided a genetic construct which at least comprises a nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions and one or more origins of replication and/or selectable marker gene sequences.

Genetic constructs are particularly suitable for the transformation of a eukaryotic cell to introduce novel genetic traits thereto, in addition to the provision of resistance characteristics to viral pathogens. Such additional novel traits may be introduced in a separate genetic construct or, alternatively, on the same genetic construct which comprises the synthetic genes herein described. Those skilled in the art will recognize the significant advantages, in particular in terms of reduced genetic manipulations and tissue culture requirements and increased cost-effectiveness of including genetic sequences which encode such additional traits and the synthetic genes described herein in a single genetic construct.

Usually, an origin of replication or a selectable marker gene suitable for use in bacteria is physically-separated from those genetic sequences contained in the genetic construct which are intended to be expressed or transferred to a eukaryotic cell, or integrated into the genome of a eukaryotic cell.

As used herein, the term "selectable marker gene" includes any gene which confers a phenotype on a cell on which it is expressed to facilitate the identification and/or selection of cells which are transfected or transformed with a genetic construct of the invention or a derivative thereof.

Suitable selectable marker genes contemplated herein include the ampicillin-resistance gene ($Amp^r$), tetracycline-resistance gene ($Tc^r$), bacterial kanamycin-resistance gene ($Kan^r$), is the zeocin resistance gene (Zeocin is a drug of the bleomycin family which is trade mark of InVitrogen Corporation), the AURI-C gene which confers resistance to the antibiotic aureobasidin A, phosphinothricin-resistance gene, neomycin phosphotransferase gen (nptII), hygromycin-resistance gene, β-glucuronidase (GUS) gene, chloramphenicol acetyltransferase (CAT) gene, green fluorescent protein-encoding gene or the luciferase gene, amongst others.

Preferably, the selectable marker gene is the nptII gene or $Kan^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as described herein, which include further genetic sequences intended for the maintenance and/or replication of said genetic construct in prokaryotes or eukaryotes and/or the integration of said genetic construct or a part thereof into the genome of a eukaryotic cell or organism.

Standard methods described supra may be used to introduce the constructs into the cell, tissue or organ, for example, liposome-mediated transfection or transformation, transformation of cells with attenuated virus particles or bacterial cells, cell mating, transformation or transfection procedures known to those skilled in the art.

Additional means for introducing recombinant DNA into plant tissue or cells include, but are not limited to, transformation using $CaCl_2$ and variations thereof, direct DNA uptake into protoplasts, PEG-mediated uptake to protoplasts, microparticle bombardment, electroporation, microinjection of DNA, microparticle bombardment of tissue explant or cells, vacuum-infiltration of tissue with nucleic acid, or in the case of plants, T-DNA-mediate transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

In a further embodiment of the present invention, the genetic constructs described herein are adapted for integration into the genome of a cell in which it is expressed. Those skilled in the art will be aware that, in order to achieve integration of a genetic sequence or genetic construct into the genome of a host cell, certain additional genetic sequences may be required. In the case of plants, left and right border sequences from the T-DNA of the *Agrobacterium tumefaciens* Ti plasmid will generally be required.

According to another aspect of the invention, there is provided a transformed plant cell containing an expression vector as broadly herein described. The term "plant cell" as used herein refers to protoplasts or other cells derived from plants, gamete-producing cells, and cells which regenerate into whole plants. Plant cells include cells in plants as well as protoplasts or other cells in culture. By "plant tissue" is meant differentiated and undifferentiated tissue derived from roots, shoots, pollen, seeds, tumour tissue, such as crown galls, and various forms of aggregations of plant cells in culture, such as embryos and calluses.

In a still further aspect, the invention provides a regenerated differentiated plant consisting of plant cells containing an expression vector as broadly herein described. Plants may conveniently be regenerated from transformed plant cells or tissues or organs on hormone-containing media and the regenerated plants may take a variety of forms, such as chimeras of transformed cells and non-transformed cells; clonal transformants (e.g. all cells transformed to contain the expression cassette); grafts of transformed and untransformed tissue (e.g. a transformed root stock grafted to an untransformed scion in citrus species). Transformed plants may be propagated by a variety of means, such as by clonal propagation or classical breeding techniques. For example, a first generation (or T1) transformed plants may be selfed to give homozygous second generation (or T2) transformed plants, and the T2 plants further propagated through classical breeding techniques.

Accordingly, yet another aspect of the invention is directed to a regenerated differentiated plant comprising a nucleic acid molecule encoding a polypeptide comprising an amino acid sequence substantially as set forth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

In a related embodiment, the present invention is directed to a regenerated differentiated plant comprising a nucleic acid molecule, wherein the nucleic acid molecule comprises a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions.

As used herein, "plant" and "differentiated plant" refer to a whole plant or plant part containing differentiated plant cell types, tissues and/or organ systems. Plantlets and seeds are also included within the meaning of the foregoing terms. Plants included in the invention are any plants amenable to transformation techniques, including angiosperms, gymnosperms, monocotyledons and dicotyledons. In a most preferred embodiment, the plant is oil-palm or a related plant.

In yet another aspect, the invention provides oil-palm harvested from a differentiated plant as broadly described above.

The nucleic acid molecule of the present invention is useful, inter alia, to distinguish embryogenic from non-embryogenic material. Accordingly, embryogenic material may be detected in vitro by screening for expression of the subject nucleic acid molecule. As defined above, expression may result in transcript or translation product or both. A range of assays may be employed to detect nucleic acid transcript or translation products. These assays are well known to those skilled in the art and particularly useful assays are described below.

Accordingly, one aspect of the present invention contemplates a method for detecting embryogenic plant material, said method comprising screening for expression of a nucleic acid molecule, said nucleic acid molecule comprising a sequence of nucleotides substantially as set forth in SEQ ID NO:1 or SEQ ID NO:3 or its complementary form, or a nucleotide sequence having at least about 71% similarity to SEQ ID NO:1 or SEQ ID NO:3 or its complementary form or a nucleotide sequence capable of hybridizing to SEQ ID NO:1 or SEQ ID NO:3 or its complementary form under low stringency conditions wherein expression of said nucleic acid molecule is indicative of the presence of embryogenic material.

Reference to "material" includes reference to cells, tissues, callus and/or organelles or related tissue. The expression "detecting" embryogenic plant material includes distinguishing between embryogenic and non-embryogenic material.

The assay may be conducted in any number of ways. For example, mRNA transcript may be detected as the expression product. In one method, Northern blot analysis may be used.

According to this embodiment, there is provided a method for detecting embryogenic plant material, said method comprising immobilizing a sample putatively containing RNA from the material to be screened on a solid support and contacting said immobilized RNA with a labelled nucleotide sequence capable of hybridizing to all or part of an mRNA transcript corresponding to the nucleotide sequence set forth in SEQ ID NO:1 or SEQ ID NO:3 or their derivatives or homologues as defined herein and then detecting the presence of said label.

The label may be any reporter molecule capable of providing an identifiable signal such as $^{32}$P, $^{35}$S, or other radionucleotide, fluorogenic molecule, enzyme or other suitable reporter molecule.

By "immobilized" means both a "dot blot" type assay or an electrophoretic assay where the total RNA is subjected to electrophoresis.

The probe is preferably a cDNA molecule including a fragment (e.g. from about 8 nucleotides in length) or whole or substantially whole length molecules corresponding to SEQ ID NO:1 or SEQ ID NO:3 or its complementary form. Alternatively, the probe is a RNA molecule complementary to the target mRNA sequence.

Any number of variations may be performed to the assay without departing from the scope or spirit of the invention.

In another embodiment, expression is determined by detecting the translation product, i.e. a sequence of amino acids such as in the form of a peptide, polypeptide or protein (encompassed herein by the term "polypeptide").

In one useful embodiment, antibodies are generated to the subject polypeptide. Such antibodies may be used in an immunoassay to detect the instant polypeptide. The presence of the polypeptide is indicative of embryogenic material.

Accordingly, another aspect of the present invention contemplates an antibody to a polypeptide, said polypeptide comprising a sequence of amino acids substantially as set froth in SEQ ID NO:2 or an amino acid sequence having at least about 71% similarity to SEQ ID NO:2, wherein said polypeptide is present in plant zygotic embryos or embryogenic callus and is substantially not present in non-embryogenic tissue.

Either monoclonal or polyclonal antibodies may be employed. The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard and Hoffman, (1981); Kohler and Milstein, (1975); (1976).

Another aspect of the present invention contemplates a method for detecting a polypeptide which is indicative of the presence of embryogenic tissue in oil-palm or related plants, said method comprising contacting the tissue or an extract thereof with an antibody specific for said polypeptide or its derivatives or homologues for a time and under conditions sufficient for an antibody-polypeptide complex to form, and then detecting said complex.

The presence of the polypeptide may be detected in any number of ways such as by Western blotting and ELISA procedures. A wide range of immunoassay techniques are available as can be seen by reference to U.S. Pat. Nos. 4,016,043, 4,424,279 and 4,018,653.

In one assay, an unlabelled antibody specific to the oil-palm polypeptide is immobilized on a solid substrate and the sample to be tested brought into contact with the bound molecule.

After a suitable period of incubation, for a period of time sufficient to allow formation of an antibody-polypeptide complex, a second antibody specific to the polypeptide, labelled with a reporter molecule capable of producing a detectable signal, is then added and incubated, allowing time sufficient for the formation of another complex of antibody-polypeptide-labelled antibody. Any unreacted material is washed away, and the presence of the polypeptide is determined by observation of a signal produced by the reporter molecule. The results may either be qualitative, by simple observation of the visible signal, or may be quantitated by comparing with a control ample containing known amounts of polypeptide. Variations on this assay include a simultaneous assay, in which both sample and labelled antibody are added simultaneously to the bound antibody. These techniques are well known to those skilled in the art, including any minor variations as will be readily apparent. In accordance with the present invention, the sample is one which might contain the oil-palm polypeptide including cell or callus extract or lysate. The sample is, therefore, generally a biological sample.

In this assay, a first antibody having specificity for the polypeptide or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to about 38° C. such as 25° C.) to allow binding of the antibody. Following the incubation period, the antibody solid phase is washed and dried and incubated with a second antibody specific for a portion of the polypeptide. The second antibody is linked to a reporter molecule which is used to indicate the binding of the second antibody to the polypeptide.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule", as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay (EIA), an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-polypeptide complex, allowed to bind, and then the excess reagent is washed away. A solution containing the appropriate substrate is then added to the complex of antibody-polypeptide-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-polypeptide complex. After washing off the unbound reagent, the remaining tertiary complex is then exposed to the light of the appropriate wavelength, the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention, therefore, provides in one embodiment, a screening procedure to identify, detect or otherwise discriminate between embryogenic and non-embryogenic material. In this regard, substantial savings in time and cost may be made by removing non-embryogenic material from tissue being used in in vitro multiplication of oil-palm or related plants. The ability to distinguish embryogenic cultures from the non-embryogenic cultures at an early stage facilitates culling of cultures and thus expensive laboratory space can be saved as well as months of labor. Furthermore, the ability to control embryogenesis would meant that cultures need not depend on random chance to attain their embryogenic potential. The assay of the present invention may also be automated or semi-automated where one or more steps are controlled by a computer programme. Alternatively or in addition, the present invention further provides a test kit for identifying embryogenic material, said test kit in compartmental form comprises in one compartment, an agent for detecting a nucleic acid or polypeptide associated with embryogenic material in oil-palm plants or related plants; a second or further compartments are adapted to contain reagents including solid supports for detecting the subject nucleic acid molecule or polypeptide.

The polypeptide of the present invention is also useful in therapeutic treatments, such as in anti-aging.

Accordingly, another aspect of the present invention contemplates a composition such as a pharmaceutical composition comprising the polypeptide having an amino acid sequence as set forth in SEQ ID NO:2 or a functional homologue thereof or a molecule having at least 71% similarity to SEQ ID NO:2 and one or more pharmaceutically acceptable carriers and/or diluents.

The preferred composition of the present invention is in the form of a pharmaceutical composition.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium mono stearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet or administered via breast milk. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules, creams and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

It is particularly advantageous to incorporate the active ingredient as a cream capable of preventing or delaying aging.

The present invention is further described by the following non-limiting Examples.

Example 1

Reverse Transcription of PCR (RT-PCR)

A one-step RT-PCR was carried out with the use of the Titan One Tube RT-PCR System from Boehringer Mannheim.

The reaction components for master mix 1 and master mix 2 were prepared in separate DEPC-treated tubes. The components in master mix 1 were: 4 µl of dNTP mix (10 mM)+1 µl downstream primer (10 µM)+1 µl upstream primer (10 µM)+1 µl template RNA (~1 µg zygotic embryo total RNA)+ 2.5 µl DTT solution (100 mM)+7 µl RNase inhibitor (40 U/µl)+sterile $H_2O$ to a final volume of 25 µl. The primers used here were the AGL15AtF (5'-AGGAGGATTGTGCAGAG-3' [SEQ ID NO:5]) and AGL15AtR (5'-CAAACTCT-CAGCTAGGCA-3' [SEQ ID NO:6]) based on Heck et al. (1995).

In master mix 2, 10 µl of the 5×RT-PCR buffer with $Mg^{2+}$ and 1 µl of the enzyme mix (AMV reverse transcriptase+ Expand High Fidelity enzyme mix) were added together in a total volume of 25 µl made up by $H_2O$. The whole 25 µl of master mix 1 and master mix 2 were added into a 0.2 ml thin-walled PCR tube on ice. The contents were mixed properly and briefly centrifuged to collect the sample at the bottom of the tube. The preparation was overlaid with 30 µl mineral oil and placed in a thermocycler, which had been equilibrated at 50° C. for 30 min, after which the programme went directly into thermocycling.

The parameters had been set at: 94° C. for 2 min; 10 cycles at (94° C. for 30 sec; 50° C. for 30 sec; 68° C. for 45 sec); 25 cycles at (94° C. for 30 sec; 50° C. for 30 sec; 68° C. for 45 sec+cycle elongation of 5 sec for each cycle); a final extension at 68° C. for 7 min. The RT-PCR product was analyzed on a 2% agarose gel. Bands were excised from the gel and purified using the Concert Rapid Gel Extraction kit (Clontech) and cloned into pCRScript (Stratagene). This cloning kit is very similar to the Zero Blunt TOPO PCR cloning kit except that clones are selected on LB+50 µg/ml ampicillin medium.

Two bands were obtained with AGL15AtF and AGL15AtR (FIG. 1). Both bands were excised, the ends were polished and they were then cloned into pCR-Script (Stratagene) and transformed into DH5α competent cells. The successfully transformed clones were designated RTPCR1 (for clone from fragment 1) and RTPCR2 (for clone from fragment 2). RTPCR1 and RTPCR2 were cultured and plasmid minipreps were done.

Example 2

Sequence Analysis

Clones to be sequenced were sent to ACGT (USA) and the sequencing was performed on a single-run basis using universal primers T3/T7 for most clones except for clones from the enriched library, where the primers PN1/PN2 were used. Sequence analyses were carried out using DNASIS (Hitachi software package, 1997) and BLAST (Basic Local Alignment Search Tool) (Altshul et al., 1990; 1997), available via the internet at http://www.ncbi.nlm.nih.gov. To analyze the sequences with their closely related counterparts, the alignment of the sequences was done using the CLUSTALW programme available from the Biology Workbench version 3.2 on line.

Both analyses gave similar results. RTPCR1 was shown to have about 71% homology (DNASIS) to an embryo specific mRNA of Bromus secalinas, which is found to be up-regulated in hydrated dormant seeds (Goldmark et al., 1992), as well as a few other dormancy related genes. RTPCR2, on the other hand was found to have a homology (>71%) to an S-phase specific gene (Uchimiya et al., 1994) which is involved in the cell cycle. Through the sequencing results, it was realized that the reason two very distinct bands were produced was because each band was generated by only one type of primer. That is, RTPCR1 by AGL15AtR and RTPCR2 by AGL15AtF.

Example 3

Northern Hybridization

The different types of poly $A^+$ RNA extracted were electrophoresed on 2% v/v formaldehyde gels and transferred onto nylon membranes using standard blotting techniques (Maniatis et al., 1982). Two percent formaldehyde gels (120 ml) were prepared by melting down 3 g of agarose in 110 ml of DEPC-treated $H_2O$ and 15 ml 10×MOPS buffer (200 mM MOPS (Ph 7.0), 10 mM EDTA, 50 mM sodium acetate). When the mixture cooled down to about 55° C., 37% formaldehyde was added to a final concentration of 6%. The contents were properly mixed and then poured into the gel casting tray and allowed to set.

In the preparation of the RNA samples for analysis, about 10 to 15 µg of total RNA was used for each different type of tissue. The RNA samples used were in a small volume of $H_2O$. At times, the samples needed to be concentrated: the maximum volume of RNA that can be accommodated was 4.8 µl for each preparation. In each tube, the required amount of RNA (if less than 4.8 µl was needed, $H_2O$ was added to a final volume of 4.8 µl) was added into 2 µl of 10×MOPS buffer, 3.2 µl of 37% formaldehyde and 10 µl of formamide, making the total volume 20 µl. The samples were placed in a heating block at 65° C. for 15 min and immediately chilled on ice. Just before loading, 2 µl of loading buffer (50% glycerol+1 mM EDTA+0.25% bromophenol blue+0.25% xylene cyanole) was added into each tube. Gels were electrophoresed in 1×MOPS buffer at a low voltage (20 to 30V) until the bromophenol blue dye reached the bottom of the gel.

The gel was stained with 0.5 µg/ml ethidium bromide in 200 mM ammonium acetate for 45 min to 1 hr. This was followed by destaining with several changes of DEPC-treated H₂O, until the bands of the RNA marker (Gibco BRL) and the rRNA of the samples were clearly visible. The individual bands of the marker were marked by making a hole in them. Similarly, the rRNA bands (28S and 18S) of the samples were also randomly marked. The gels were rinsed with DEPC-treated H₂O and several times to remove the formaldehyde, followed by a final rinse with 2×SSC before blotting. The gel was placed on its reverse side on the blotting apparatus, making sure that no bubbles were trapped in between the gel and the wick, which was made of 2 pieces of 3MM Whatman chromatography paper that had been cut to size. The wick forms a bridge on a glass plate placed across a container with 10×SSC as the transfer buffer. A positively charged nylon membrane was cut to size, along with 4 pieces of 3MM Whatman chromatography paper of the same size, and pre-wetted in 2×SSC. First, the wet membrane was placed carefully onto the gel, without trapping any air bubbles, and this was followed by the pre-wetted paper. Another 4 pieces of dry 3MM Whatman chromatography paper and a stack of paper towels were placed over this. A glass plate was placed right at the top of this set-up and weights were added to keep them in direct contact with each other. The transfer was allowed to occur for at least 16 hr.

After the transfer was completed, the blotting set-up was dismantled and the marks previously made on the gel were penciled onto the membrane. The membrane was then rinsed in 2×SSC for 15 min and auto-crosslinked at 120,000 µJ of UV energy or alternatively baked at 80° C. for 1.5 to 2 hr.

The probes were radioactively labeled using the High Prime kit (Boehringer Mannheim). As a control, 18S rRNA probe was also hybridized to the RNA blots. The 18S rRNA probe was prepared by double-digesting the pBG35 plasmid (Malaysian Palm Oil Board) with Kpn1 (Promega) and EcoR1 (Promega) at 37° C. overnight. The digest contained 1.0 µl plasmid pBG35, 2.0 µl 10× restriction buffer, 1.5 µl EcoR1 (12 U/µl), 1.5 µl Kpn1 (12 U/µl) and sterile H₂O to a final volume of 20 µl. The digestion was electrophoresed on a 0.8% agarose gel and the desired 1.6 kb band was excised from the gel and purified. Usually in the case of Northern analysis, high stringency washes were applied (up to 0.5× SSC+0.1% SDS at 65° C. for 15 min).

Figure 1B:
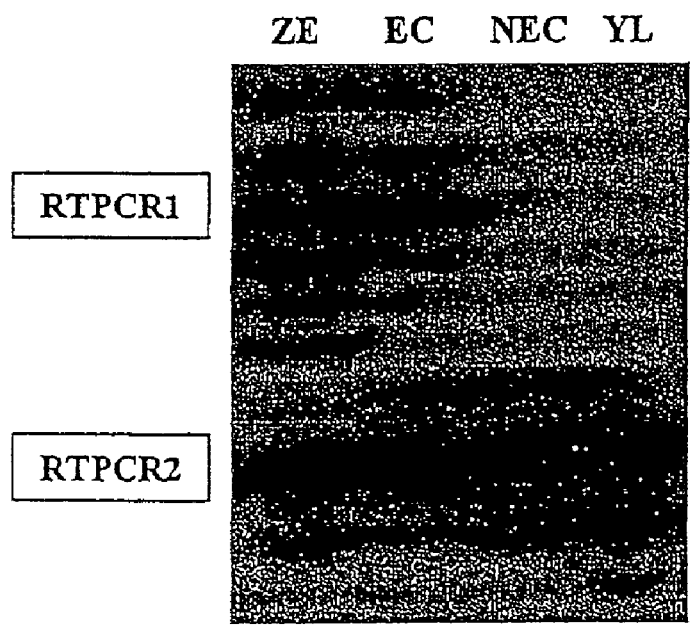
FIG. 1b is a photographic representation showing Northern analysis of RTPCR1 and RTPCR2. RTPCR1 was exclusively expressed in embryogenic materials (ZE and EC). However, RTPCR2 was constitutively expressed. ZE: zygotic embryo; EC: embryogenic calli; NEC: non-embryogenic calli; YL: young leaves.

An initial, simple Northern analysis was carried out on the two RTPCR clones and interestingly, RTPCR1 was found to be expressed only in zygotic embryo (ZE) and embryogenic callus (EC), indicating that it may be an embryogenic related gene. By comparison, RTPCR2 was constitutively expressed (FIG. 1b).

Example 4

(a) Further Characterization

Sequence of Full-Length Clone

Because of the interesting results obtained with RTPCR1, this clone was further studied. RTPCR1 was only of partial length when obtained through RT-PCR, therefore the zygotic embryo cDNA library was screened to obtain its full-length clone. The resultant clone was named as OPEm1. The nucleotide and deduced amino acid sequences of OPEm1 is shown in FIG. 3. It contains an open reading frame (ORF) from position 30 to 605 encoding a protein with 192 amino acids. A hydrophobic region occurs close to the carboxyl-terminus of the predicted protein, which has a predicted pI of 7.48 (FIG. 2b).

(b) Detailed Northern Analysis

Figure 2A:
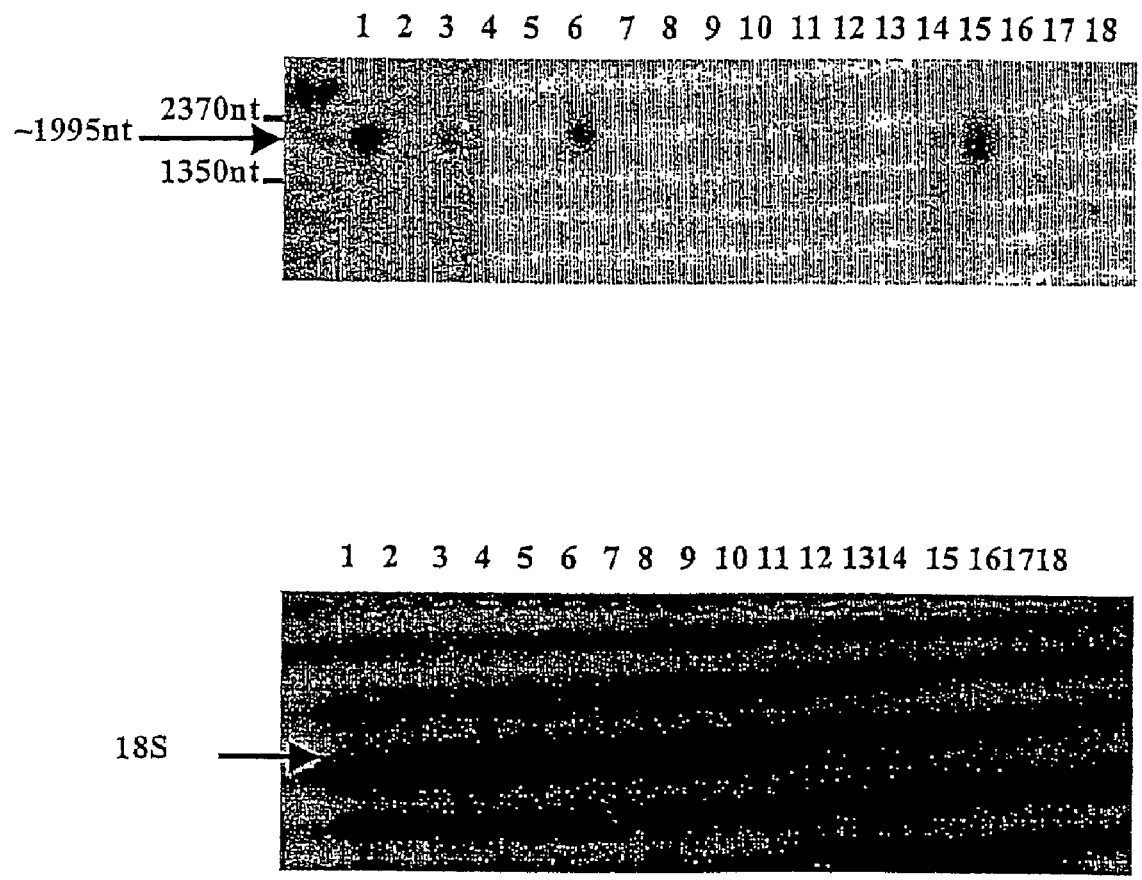
FIG. 2a is a photographic representation showing Northern analysis of OPEm1 (top) and expression of 18S ribosomal cDNA (bottom) as control. Each lane contains 10 µg of total RNA from different types of tissues. Lane 1: embryogenic calli from clone FC1454; Lane 2: embryogenic calli of clone FC1454 that have lost their embryogenic potential (ENP); Lane 3: embryogenic calli from FC1501; Lane 4: ENP of FC1501; Lane 5: Non-embryogenic calli of FC1501. Lane 6: embryogenic calli of FC1509; Lane 7: ENP of FC1509; Lane 8: non-embryogenic calli of FC1509; Lane 9: embryogenic calli from early suspension cultures; Lane 10: suspension cultures; Lane 11: white embryoids; Lane 12: green embryoids; Lane 13: bipolar structures; Lane 14: immature 12 WAA zygotic embryos; Lane 15: mature 15 WAA zygotic embryos; Lane 16: vegetative meristem; Lane 17: inflorescence from frond 17 and Lane 18: young leaves.
Figure 2B:
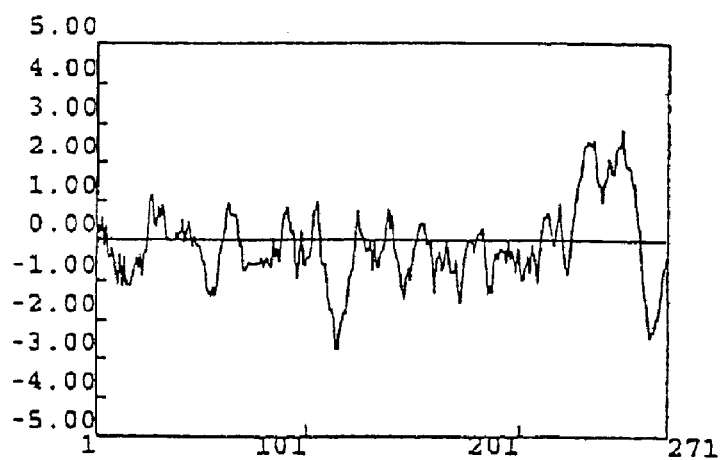
FIG. 2b is a graphical representation showing hydropathy plot of OPEm1 with a calculated pI of 7.48.

A more detailed Northern blot was prepared to reconfirm the previous results obtained (FIG. 2a). The transcript size of OPEm1 was determined to be approximately 1995 nucleotides (nt). The expression pattern of OPEm1 further proves that this clone has the potential to be exploited as an embryogenic marker because its expression can be detected in all the embryogenic calli regardless of their clonal differences, in suspension cultures. (lanes 9 and 10), in embryoids (lanes 11 and 12) right up to somatic embryos in the form of bipolar structures (lane 13). Expression signals in lanes 9, 10 and 13 are a little faint but were still able to be visibly detected on the autoradiograph. Expression was also detected in zygotic embryo (lane 15). The expression of OPEm1 was not found in cultures that had lost their embryogenic potential (lanes 2, 4 and 7), non-embryogenic calli (lanes 5 and 8) as well as other vegetative tissues such as the meristem, inflorescences and young unexpended leaves of the oil-palm (lanes 16, 17 and 18 respectively).

Example 5

Southern Hybridization

Genomic DNA of the oil-palm extracted from young unexpanded leave. The genomic DNA (5 to 10 µg) was digested with several different enzymes. Each digestion contained 30 µl of genomic DNA (10 µg), 5 µl of 10× restriction buffer, 5 µl of BSA (1 mg/ml), 5 µl enzyme (EcoR1, BamH1, Hind III, Kpn1, Not1, Sfi1, Spe1 and Stu1) and sterile H₂O to a final volume of 50 µl. The digestion was carried out at 37° C. and complete digestion was ensured by an overnight incubation. The digested DNA was electrophoresed on a 1.0% agarose gel along side a 1 kb DNA molecular weight marker (Promega). After the run, the gel was photographed and holes were made to mark the positions of the bands belonging to the marker. The gel was then immersed in depurination solution (0.25 N HCl) for 10 min with gentle shaking. The solution was decanted and the gel was rinsed several times with sterile H₂O, after which denaturation solution (0.5 M NaOH, 1.5 M NaCl) was added to the gel and agitated for 30 min. This was again followed by several rinses of sterile H₂O and finally the gel was neutralized with the neutralization solution (3 M NaCl, 0.5 M Tris-HCl (Ph 7.4)) for 30 min.

Figure 2C:
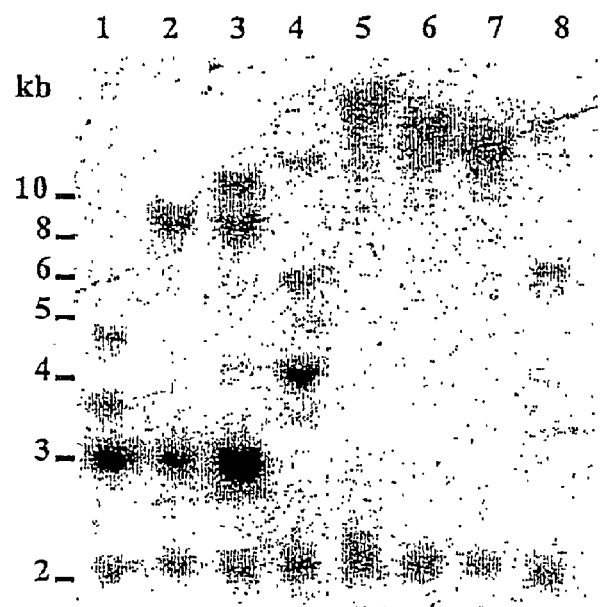
FIG. 2c is a photographic representation showing Southern analysis of OPEm1. Each lane contains 10 µg genomic DNA digested with: Lane 1: EcoRI; Lane 2: BamHI; Lane 3: HindIII; Lane 4: KpnI; Lane 5: NcoI; Lane 6: SfiI; Lane 7: SpeI and Lane 8: StuI. The digests were run alongside a 1 kb DNA molecular weight marker (Promega).

A similar blotting apparatus as for the Northern was set up for Southern analysis. Southern analysis showed that OPEm1 gene may be a member of a multigene family (FIG. 2c).

Example 6

3D-Structure

Figure 4A:
FIG. 4a is photographic representation showing a 3-D structure of the monomer unit of the human peroxiredoxin, C91S-hORF6. Each monomer consists of 224 amino acids with two domains. Domain I is the larger N-terminal domain and Domain II is the smaller C-terminal domain.

Since the results of the Northern analyses seems to contradict the function inferred for the gene based on its sequence similarity to dormancy-related genes, it was decided that the protein structure of OPEm1 should be determined, in order to try to elucidate the possible function of the gene. FIG. 4a represents the 3-dimensional (3D) structure predicted for OPEm1 and it was evident that it had a very similar structure to the monomer unit of a human peroxiredoxin (Choi et al., 1998). The human peroxiredoxin (Prx), C19S-hORF6, exists in the form of a homodimer (FIG. 4c).

Figure 4B:
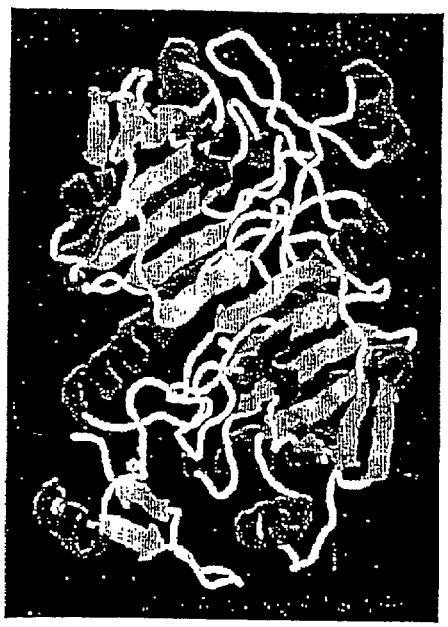
FIG. 4b is a photographic representation showing that human peroxiredoxin exists as a tightly associated dimer.
Figure 4C:
FIG. 4c is a photographic representation showing the deduced 3-D structure of OPEm1, which has very high similarity to the human peroxiredoxin.
Figure 4D:
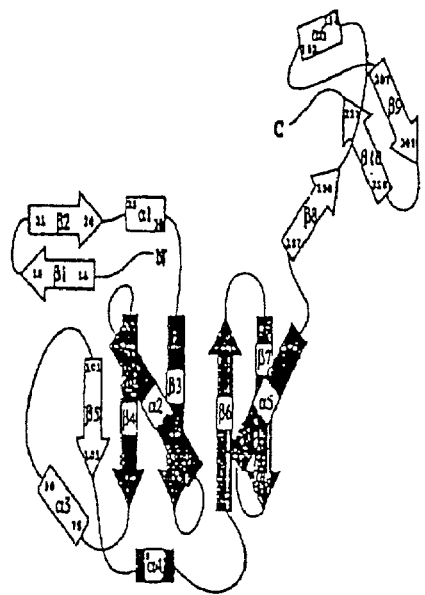
FIG. 4d is a schematic representation depicting a topology diagram of C91S-hORF6 monomer. The shaded area corresponds to the thioredoxin fold.

The structure of OPEm1 can be explained based on the 3D structure and topology diagram of the C19S-hORF6 which is shown in FIGS. 4b and 4d, respectively. The monomer can be divided into two domains, D1 and D2. D1, the larger of the two, is the N-terminal, which contains the thioredoxin fold (active site of the enzyme). This site has a βαβ motif comprised of four-stranded β-sheets (β3, β4, β6 and β7) and three flanking α-helices (α2, α4 and α5). There are also two β-strands (β1 and β2) and a short α-helix (α1) at the N-terminus just before the thioredoxin fold. After the βαβ motif, an α-helix (α3) and a β-strand (β5) are inserted. In the case of the C19S-hORF6, D2 comprises three β-strands and one α-helix and it is connected to D1 by the extended helix α5 and a following loop. In OPEm1, this region is very short, having only two β-sheets (8β and 9β) with a loop between them. This difference is also reflected in FIG. 6, in which, by residue 189, their amino acid sequences no longer show similarity with the group.

Example 7

Sequence Alignments

The deduced amino acid sequence of OPEm1 was compared with other plant Prx sequences that have been isolated. FIG. 5 shows the alignment of amino acid sequences 1-Cys and 2-Cys groups of Prx in plants. It seems that OPEm1 is more closely related to 1-Cys rather than to the 2-Cys group of Prx. This is reflected in FIG. 6, which shows an alignment between OPEm1 and other 1-Cys Prx in plants. They share similar sequences surrounding the first cysteine, which also sets the 1-Cys apart from the 2-Cys group. In 1-Cys, the sequences are PVCT, whereas in 2-Cys, they are represented by FVCP. From FIG. 6, it was also observed that OPEm1's C-terminus differs from the other 1-Cys Prx group. Based on the hydropathy plot (FIG. 2b), OPEm1 may be membrane bound at this region, unlike the other 1-Cys members. However, the same region in 1-Cys Prx members indicates the presence of a nuclear localization signal that facilitates the nuclear targeting function of the protein that is missing from OPEm1.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Ahee, J., Arthuis, P., Cas, J., Duval, Y., Guenin, G., Hanower, J., Hanower, P., Lievoux, D., Loiret, C., Malaurie, B., Pannetier, C., Raillot, D., Varechon, C. and Zuckerman, L. (1981). Vegetative propagation of the oil palm in vitro by somatic embryogenesis. *Oleagineux* 36: 113-115.

Altschul, S. F., Madden, T. L., Schaffer, A. A., Zhang, J., Zhang, Z., Miller, W. and Lipman, D. J. (1997). Gapped BLAST and PSI-BLAST: A New Generation of Protein Database Search Programs. *Nucleic Acids Research* 25: 3389-3402.

Altschul, S. F., Gish, W., Miller, W., Myers, E. W. and Lipman, D. J. (1990). Basic Local Alignment Search Tool. *Journal of Molecular Biology* 215: 403-410.

Ausubel et al., "Current Protocols in Molecular Biology" John Wiley & Sons Inc, 1994-1998, Chapter 15.

Bonner and Laskey (1974) *Eur. J. Biochem.* 46: 83.

Choi, H. J., Kang, S. W., Yang, C. H., Rhee, S. G. and Ryu, S. E. (1998). Crystal structure of a novel human peroxidase enzyme at 2.0 A resolution. *Nature Structural Biology* 5(5): 400-406.

Douillard and Hoffman, Basic Facts about Hybridomas, in *Compendium of Immunology* Vol. II, ed. by Schwartz, 1981

Dudits, D., Gyorgyey, J., Bogre, L. and Bako, L. (1995). Molecular Biology of Somatic Embryogenesis. In: In vitro Embryogenesis in Plants. Current Plant Science and Biotechnology in Agriculture. Thorpe, T. A. (ed.). Kluwer Academic Publishers, pp. 267-308.

Goldmark, P. J., Curry, J., Morris, C. F. and Walker-Simmons, M. K. (1992). Cloning and expression of an embryo-specific mRNA up-regulated in hydrated dormant seeds. *Plant Molecular Biology* 19(3): 433-441.

Heck, G. R., Perry, S. E., Nichols, K. W. and Fernandez, D. E. (1995). AGL15, a MADS domain protein expressed in developing embryos. *Plant Cell* 7: 1271-1282.

Jones, L. H. (1974). Propagation of clonal oil palms by tissue culture. *Oil Palm News* 17: 1-8.

Kohler and Milstein (1975) *Nature* 256: 495-499.

Kohler and Milstein (1976) *European Journal of Immunology* 6: 511-519.

Marmur and Doty (1962) *J. Mol. Biol.* 5: 109.

Pannetier, C., Arthuis, P. and Lievoux, D. (1981). Neoformation of young *Elaeis guineensis* plants from primary calluses obtained from leaf fragments cultured in vitro. *Oleagineux* 36: 119-122.

Sambrook, J., Fritsch, E. F. and Maniatis, T. (1989). Molecular Cloning: A Laboratory Manual, 2nd Ed., Cold Spring Harbor Laboratory Press, New York.

Schwendiman, J., Pannetier, C. and Michaux-Ferriere, N. (1988). Histology of somatic embryogenesis from leaf explants of the oil palm *Elaeis guineensis*. *Annals of Botany* 62: 43-52.

Turnham, E. and Northcote, D. H. (1982). The use of acetyl-CoA carboxylase activity and changes in wall composition as measures of embryogenesis in tissue cultures of oil palm (*Elaeis guineensis*). *Biochemical Journal* 208: 323-332.

Uchimiya, H., Kidou, S. I., Tsuge, T., Kato, A. and Umeda, M. (1994). Isolation and characterization of a rice cDNA similar to the S-phase-specific cyc07-gene. *Plant Molecular Biology* 24: 545-547.

Wooi, K. C. (1995). Oil palm tissue culture—current practice and constraints. In: Proceedings of the 1993 ISOPB International Symposium on Recent Developments in Oil Palm Tissue Culture and Biotechnology. Rao, V., Henson, I. E. and Rajanaidu, N. (eds.). Palm Oil Research Institute of Malaysia, Kuala Lumpur, pp. 21-32.

The invention claimed is:

1. An isolated nucleic acid molecule encoding a polypeptide comprising the amino acid sequence as set forth in SEQ ID NO: 2.

2. The isolated nucleic acid molecule of claim 1, wherein said nucleic acid molecule comprises the sequence of nucleotides as set forth in SEQ ID NO: 1 or SEQ ID NO: 3 or its complementary form.

3. The isolated nucleic acid molecule of claim 1, wherein the nucleic acid molecule comprises the nucleotide sequence as set forth in SEQ ID NO: 1.

4. The isolated nucleic acid molecule of claim 1, wherein the nucleic acid molecule comprises the nucleotide sequence as set forth in SEQ ID NO: 3.

5. A genetic construct comprising a nucleic acid molecule encoding a polypeptide comprising the amino acid sequence as set forth in SEQ ID NO: 2.

6. The genetic construct of claim 5, wherein the nucleic acid molecule comprises the nucleotide sequence as set forth in SEQ ID NO: 1 or SEQ ID NO: 3 or its complementary form.

7. The genetic construct of claim 5, wherein the nucleic acid molecule comprises the sequence of nucleotides as set forth in SEQ D NO: 1.

8. The genetic construct of claim 5, wherein the nucleic acid molecule comprises the sequence of nucleotides as set forth in SEQ ID NO: 3.

9. The genetic construct of claim 5 or 6, wherein said construct further comprises one or more promoter sequences or transcription termination sequences.

10. The genetic construct of claim 9, wherein said construct further comprises one or more origins of replication and/or selectable marker gene sequences.

11. A vector comprising the construct of any one of claims 5-6 or 7-8.

12. A host cell comprising an isolated nucleic acid molecule encoding a polypeptide comprising the amino acid sequence as set forth in SEQ ID NO: 2, wherein the isolated nucleic acid molecule is introduced into the host cell.

13. The host cell of claim 12, wherein said nucleic acid molecule comprises the sequence of nucleotides as set forth in SEQ ID NO: 1 or SEQ ID NO: 3 or its complementary form.

14. The host cell of claim 12, wherein the nucleic acid molecule comprises the nucleotide sequence as set forth in SEQ ID NO: 1.

15. The host cell of claim 12, wherein the nucleic acid molecule comprises the nucleotide sequence as set forth in SEQ ID NO: 3.

16. The host cell of claim 12, wherein the cell is a plant cell.

17. The plant cell of claim 16, wherein the cell is from an oil-palm plant.

18. A method for producing a recombinant polypeptide in a host cell or tissue, said method comprising introducing into the said cell or tissue an expression vector comprising the nucleic acid molecule of claim 1 or 2, wherein said nucleic acid molecule is operably linked to one or more regulatory sequences such that the nucleic acid molecule is capable of being expressed in said cell or tissue.

19. The method of claim 18, wherein said nucleic acid molecule comprises the sequence of nucleotides as set forth in SEQ ID NO: 1.

20. The method of claim 18, wherein said nucleic acid molecule comprises the sequence of nucleotides as set forth in SEQ ID NO: 3.

21. A method for detecting embryogenic plant material, said method comprising immobilizing a sample containing RNA from the material to be screened on a solid support and contacting said immobilized sample with a labeled nucleic acid molecule which comprises the nucleotide sequence set forth in SEQ ID NO: 1 or SEQ ID NO: 3, and then detecting the presence of said label.

22. A method of claim 21, wherein said nucleotide sequence is as set forth in SEQ ID NO: 1.

23. A method of claim 21, wherein said nucleotide sequence is as set forth in SEQ ID NO: 3.

* * * * *

UNITED STATES PATENT AND TRADEMARK OFFICE
CERTIFICATE OF CORRECTION

PATENT NO. : 7,745,111 B2
APPLICATION NO. : 10/028346
DATED : June 29, 2010
INVENTOR(S) : Meilina O. Abdullah et al.

Page 1 of 1

It is certified that error appears in the above-identified patent and that said Letters Patent is hereby corrected as shown below:

(Column 6, Line 48) should read dIII; Lane 4: KpnI; Lane 5: NotI; Lane 6: SfiI; Lane 7: SpeI (Column 7, Line 9) should read *campestris* L. ssp. *pekinensis,* chinese cabbage) (SEQ ID NO: 9).

(Column 18, Line 55) should read neomycin phosphotransferase gene (nptII), hygromycin-resis- (Column 21, Line 31) should read forth in SEQ ID NO:2 or an amino acid sequence having at (Column 23, Lines 29-30) should read cates the presence of the hapten of interest. Immunofluorescence and EIA techniques are both very well established in (Column 23, Line 46) should read the ability to control embryogenesis would mean that cul- (Column 41, Line 35) (Claim 7, Line 3) should read forth in SEQ ID NO: 1.

Signed and Sealed this
Tenth Day of January, 2012

David J. Kappos
*Director of the United States Patent and Trademark Office*